United States Patent
Mitchell et al.

(10) Patent No.: US 6,490,339 B2
(45) Date of Patent: Dec. 3, 2002

(54) METHOD AND APPARATUS FOR OSTEOPOROSIS SCREENING

(75) Inventors: Christopher R. Mitchell, Pleasanton, CA (US); Joseph R. Rimsa, Milpitas, CA (US); Edward P. Donlon, San Jose, CA (US); Gregory A. Sprehn, Livermore, CA (US)

(73) Assignee: Alara, Inc., Hayward, CA (US)

( * ) Notice: Subject to any disclaimer, the term of this patent is extended or adjusted under 35 U.S.C. 154(b) by 0 days.

(21) Appl. No.: 10/007,815

(22) Filed: Nov. 9, 2001

(65) Prior Publication Data

US 2002/0067799 A1 Jun. 6, 2002

Related U.S. Application Data

(63) Continuation of application No. 09/481,299, filed on Jan. 11, 2000.

(51) Int. Cl.[7] ............................................. G01N 23/04
(52) U.S. Cl. ............................................................. 378/62
(58) Field of Search .............................. 378/62, 50, 54, 378/195, 208, 209, 210; 250/584, 585, 586, 589

(56) References Cited

U.S. PATENT DOCUMENTS

| 4,674,110 A | 6/1987 | Eaton et al. ............... 378/208 |
| 4,721,112 A | 1/1988 | Hirano et al. ............. 128/659 |
| 4,736,102 A | 4/1988 | Morrone ................... 250/327.2 |

(List continued on next page.)

FOREIGN PATENT DOCUMENTS

| CA | 2178397 | 7/1996 | ............ A61B/6/03 |
| CA | 2205514 | 11/1997 | ............ A61B/6/02 |
| DE | 196 09 138 A1 | 9/1996 | ............ A61B/6/03 |
| EP | 0 077 678 A2 | 4/1983 | ............ G03B/35/14 |
| EP | 0 724 167 A1 | 7/1996 | ............ G01T/1/29 |
| EP | 0 747 008 A1 | 12/1996 | ............ A61B/6/00 |
| EP | 0 757 251 A2 | 2/1997 | ............ G01N/33/566 |
| EP | 0 724 167 B1 | 9/1997 | ............ G01T/1/29 |
| EP | 0 867 147 A1 | 9/1998 | ............ A61B/8/08 |
| JP | 1-241536 | 9/1989 | ............ G03B/42/02 |
| WO | WO 88/00697 | 1/1988 | ............ G01N/23/04 |
| WO | WO 96/35372 | 11/1996 | ............ A61B/6/14 |
| WO | WO 97/31335 | 8/1997 | ............ G06T/5/40 |
| WO | WO 97/42874 | 11/1997 | ............ A61B/6/00 |
| WO | WO 97/48988 | 12/1997 | ............ G01T/1/24 |
| WO | WO 98/34100 | 6/1998 | ............ G01N/23/00 |

OTHER PUBLICATIONS

Liu, B. et al., "Automatic segmentation of bones from digital hand radiographs", *SPIE*, Feb. 27–Mar. 2, 1995, vol. 2434 0–8194–1782–Mar. 1995, pp. 659–669.

Hyeonjoon, S. et al., "Object–oriented approach towards the automatic segmentation of bones from pediatric hand radiographs", *SPIE*, Feb. 25–Feb. 28, 1997, vol. 3034 0277–786X/97, pp. 95–105.

*Primary Examiner*—David P. Porta
*Assistant Examiner*—Courtney Thomas
(74) *Attorney, Agent, or Firm*—Paul Davis; Heller Ehrman White & McAuliffe

(57) ABSTRACT

A method and apparatus for forming and reading a radiation image of an object is provided. The method is performed by placing an object of which a radiation image is to be taken adjacent a platform that is positioned between a storage layer radiation screen and an electromagnetic wave radiation source such that radiation from the electromagnetic wave radiation source which traverses the object is absorbed by the storage layer radiation screen; forming a latent radiation image of the object on the storage layer radiation screen by causing the electromagnetic wave radiation source to emit radiation, a portion of the emitted radiation traversing the object and being absorbed by the storage layer radiation screen; and reading the latent radiation image of the object from the storage layer radiation screen.

17 Claims, 31 Drawing Sheets

U.S. PATENT DOCUMENTS

| | | | | |
|---|---|---|---|---|
| 4,771,272 | A | 9/1988 | Barnes | 340/624 |
| 4,792,691 | A | 12/1988 | Morlotti et al. | 250/484.1 |
| 4,792,900 | A | 12/1988 | Sones et al. | 364/413.23 |
| 4,829,549 | A | 5/1989 | Vogel et al. | 378/55 |
| 4,845,731 | A | 7/1989 | Vidmar et al. | 378/98 |
| 4,903,203 | A | 2/1990 | Yamashita et al. | 364/413.15 |
| 4,975,935 | A | 12/1990 | Hillen et al. | 378/28 |
| 4,986,273 | A | 1/1991 | O'Neill et al. | 128/653 R |
| 5,024,791 | A | 6/1991 | Cusano et al. | 264/21 |
| 5,084,619 | A | 1/1992 | Pfeiler et al. | 250/327.2 |
| 5,132,995 | A | 7/1992 | Stein | 378/56 |
| 5,138,553 | A | 8/1992 | Lanza et al. | 364/413.26 |
| 5,150,394 | A | 9/1992 | Karellas | 378/62 |
| 5,235,528 | A | 8/1993 | Silver et al. | 364/571.07 |
| 5,235,628 | A | 8/1993 | Kalender | 378/207 |
| 5,241,406 | A | 8/1993 | Johnston et al. | 358/487 |
| 5,247,559 | A | 9/1993 | Ohtsuchi et al. | 378/53 |
| 5,247,560 | A | 9/1993 | Hosokawa et al. | 378/54 |
| 5,253,282 | A | 10/1993 | Pelc | 378/99 |
| 5,270,530 | A | 12/1993 | Godlewski et al. | 250/208.1 |
| 5,270,651 | A | 12/1993 | Wehrli | 324/308 |
| 5,272,760 | A | 12/1993 | Echerer et al. | 382/6 |
| 5,276,328 | A | 1/1994 | Yoshida et al. | 250/368 |
| 5,280,512 | A | 1/1994 | Maack et al. | 378/29 |
| 5,291,537 | A | 3/1994 | Mazess | 378/54 |
| 5,305,368 | A | 4/1994 | Bisek et al. | 378/146 |
| 5,335,260 | A | 8/1994 | Arnold | 378/207 |
| 5,343,863 | A | 9/1994 | Wiener et al. | 128/660.01 |
| 5,349,959 | A | 9/1994 | Wiener et al. | 128/660.06 |
| 5,365,564 | A | 11/1994 | Yoshida et al. | 378/55 |
| 5,381,245 | A | 1/1995 | Johnston et al. | 358/487 |
| 5,384,862 | A | 1/1995 | Echerer et al. | 382/6 |
| 5,418,373 | A | 5/1995 | Shimura | 250/583 |
| 5,426,709 | A | 6/1995 | Yoshida et al. | 382/132 |
| 5,434,431 | A | 7/1995 | Verbeke et al. | 250/585 |
| 5,481,587 | A | 1/1996 | Mazess | 378/207 |
| 5,483,965 | A | 1/1996 | Wiener et al. | 128/661.03 |
| 5,509,042 | A | 4/1996 | Mazess | 378/54 |
| 5,533,080 | A | 7/1996 | Pelc | 378/5 |
| 5,533,084 | A | 7/1996 | Mazess | 378/54 |
| 5,536,946 | A | 7/1996 | Vuylsteke | 250/586 |
| 5,548,126 | A | 8/1996 | Exelmans et al. | 250/588 |
| 5,574,803 | A | 11/1996 | Gaborski et al. | 382/259 |
| 5,575,952 | A | 11/1996 | Keogh et al. | 252/404 |
| 5,583,663 | A | 12/1996 | Boeve | 358/487 |
| 5,590,167 | A | 12/1996 | Arai | 378/38 |
| 5,603,325 | A | 2/1997 | Mazess et al. | 128/660.06 |
| 5,629,968 | A | 5/1997 | Trauernicht | 378/98.8 |
| 5,646,417 | A | 7/1997 | Dewaele et al. | 250/584 |
| 5,657,369 | A | 8/1997 | Stein et al. | 378/208 |
| 5,671,070 | A | 9/1997 | Przybylowicz et al. | 358/487 |
| 5,673,298 | A | 9/1997 | Mazess | 378/54 |
| 5,687,211 | A | 11/1997 | Berger et al. | 378/196 |
| 5,693,954 | A | 12/1997 | Jacobs et al. | 250/581 |
| 5,696,805 | A | 12/1997 | Gaborski et al. | 378/54 |
| 5,712,892 | A | 1/1998 | Weil et al. | 378/54 |
| 5,715,820 | A | 2/1998 | Stein et al. | 128/653.1 |
| 5,717,735 | A | 2/1998 | Ramsdell et al. | 378/208 |
| 5,729,587 | A | 3/1998 | Betz | 378/198 |
| 5,734,740 | A | 3/1998 | Benn et al. | 382/132 |
| 5,748,704 | A | 5/1998 | Mazess et al. | 378/54 |
| 5,748,705 | A | 5/1998 | Stein et al. | 378/196 |
| 5,748,768 | A | 5/1998 | Sivers et al. | 382/130 |
| 5,757,021 | A | 5/1998 | Dewaele | 250/581 |
| 5,772,592 | A | 6/1998 | Cheng et al. | 600/407 |
| 5,778,045 | A | 7/1998 | von Stetten et al. | 378/98.9 |
| 5,785,656 | A | 7/1998 | Chiabrera et al. | 600/449 |
| 5,834,782 | A | 11/1998 | Schick et al. | 250/370.11 |
| 5,835,555 | A | 11/1998 | Barry et al. | 378/146 |
| 5,835,562 | A | 11/1998 | Ramsdell et al. | 378/206 |
| 5,840,029 | A | 11/1998 | Mazess et al. | 600/437 |
| 5,841,832 | A | 11/1998 | Mazess et al. | 378/56 |
| 5,841,833 | A | 11/1998 | Mazess et al. | 378/98.9 |
| 5,852,647 | A | 12/1998 | Schick et al. | 378/53 |
| 5,886,353 | A | 3/1999 | Spivey et al. | 250/370.09 |
| 5,898,753 | A | 4/1999 | Schick et al. | 378/54 |
| 5,910,792 | A | 6/1999 | Hansen et al. | 345/77 |
| 5,910,972 | A | 6/1999 | Ohkubo et al. | 378/54 |
| 5,917,877 | A | 6/1999 | Chiabrera et al. | 378/5.3 |
| 5,917,929 | A | 6/1999 | Marshall et al. | 382/128 |
| 5,949,846 | A | 9/1999 | Stein et al. | 378/54 |
| 6,246,745 | B1 | 6/2001 | Bi et al. | 378/54 |
| 6,320,931 | B1 * | 11/2001 | Arnold | 378/54 |

* cited by examiner

FIG. 8D

Expose

Operator ID: 1234
Patient ID: 123-45-6789
Patient Age: 59
Patient Gender: Female
Patient Ethnicity: Asian
Black
Caucasion
Hispanic

Back
Select
Enter

Expose (9) (6>) (3) (v-)
(^8) (5) (2v) (.)
(7) (<4) (1) (0)

○ ○ ○ ○ ○

Operator ID: 1234

Patient ID: 123-45-6789

Patient Age: 59

Patient Gender: Female

Patient Ethnicity: Caucasion

*Modify Entries*

*Accept Entries*

FIG. 8E

METHOD AND APPARATUS FOR OSTEOPOROSIS SCREENING

This application is a continuation of U.S. application Ser. No. 09/481,299, filed on Jan. 11, 2000, which is incorporated herein by reference in its entirety.

BACKGROUND OF THE INVENTION

1. Field of the Invention

This invention relates to a method and apparatus for measuring bone mineral density and may be used for osteoporosis screening. More specifically, the invention relates to a method and apparatus for measuring bone mineral density using electromagnetic wave radiation and storage layer radiation screens.

2. Description of Related Art

Osteoporosis is a bone disease in which bones become thinner and more porous, commonly resulting in fractures of the bones. More than 1.5 million osteoporosis-related fractures occur each year in the United States, usually in the spine, hip and wrist. Osteoporosis is most common in older women and about 25% of women older than 60 years have osteoporosis.

Bone density testing, which measures bone mineral content, is used to diagnose osteoporosis. A low bone density may indicate a risk for fractures in the future. The test can also be used to determine a rate of bone mineral loss in those not receiving treatment, and a rate of bone gain in those being treated.

Several different methods and apparatuses have been developed for measuring bone mineral density. These different methods and apparatuses can be broadly divided based on whether they are single or dual energy X-ray systems.

Mineral loss in a person's bones can be estimated from a single X-ray image of a body part. One potential difficulty associated with single X-ray images is that it is difficult to determine how much of the X-ray image is due to hard tissue (e.g., bones) and how much is due to soft tissue (skin, muscle, ligaments, etc.).

Dual-energy x-ray absorptometry (DXA) is a technique which has been developed which uses two x-ray images obtained using x-rays of different energy levels to compensate for the fact that hard tissue is surrounded by soft tissue that also contributes to an x-ray image. Dual energy systems use two images to obtain a set of two simultaneous equations for each pixel in the images and then solve those equations to determine the amount of x-rays that was absorbed by the bone. Shimura (U.S. Pat. No. 5,187,731) describes a method for quantifying bone mineral using a dual energy radiation system.

The two x-ray images are obtained using x-rays with different energy levels to compensate for tissue variations in quantifying bone mass in an x-ray image. Typically, existing DXA systems rely on known x-ray absorption characteristics of hard tissue and soft tissue to both high-energy and low-energy radiation. Some systems use an x-ray image of a wedge of material with bone-like x-ray attenuation properties (e.g., aluminum) to calibrate the system, where the thickness and density of each part of the wedge is known in advance.

Existing DXA measurements generally require expensive equipment that is usually available only in specialized facilities. This equipment is typically complex, and the test results must be interpreted by a skilled person (e.g., a radiographer), resulting in significant cost of labor. In addition, because the test results must be interpreted by humans, existing tests are not highly repeatable. It would be advantageous to remove human variations and determine more accurately the progression of osteoporotic condition over a period of time, such as one year intervals, to determine the progression of bone loss. The need for the interpretation of test results also makes it more difficult to return these results to the patient instantly.

U.S. Pat. Nos. 5,150,394 and 5,465,284 describe systems which measure bone density using x-ray radiation at two different energy levels. In these patents, x-ray radiation of two intensity levels is transmitted through a portion of the patients body to a scintillator which converts the x-rays into visible light. The visible light emitted by the scintillator is provided to a charge-coupled device (CCD), which in turn converts the visible light into an electrical signal. The system then forms an image of the body from the electrical signal, and determines the density the patient's bone from the image.

U.S. Pat. Nos. 5,852,647 and 5,898,753 also describe dual energy level systems. In U.S. Pat. No. 5,898,753, a system is described which uses CMOS wafers instead of CCD wafers which allows larger sensors to be manufactured more readily.

SUMMARY OF THE INVENTION

The present invention relates to apparatuses and methods for forming and reading a radiation image of an object.

In one embodiment, an apparatus is provided for forming and reading a radiation image of an object which comprises: a platform adjacent to which may be placed an object of which a radiation image is to be taken; a cylindrically shaped rotatable drum; a storage layer radiation screen mounted adjacent a surface of the rotatable drum; an electromagnetic wave radiation source positioned relative to the storage layer radiation screen and the platform such that radiation from the electromagnetic wave radiation source which traverses the platform and the object adjacent the platform is absorbed by the storage layer radiation screen; an image acquisition optical system positioned adjacent the drum, the image acquisition optical system including an excitation system for directing an excitation beam in the direction of the drum, the excitation beam causing energy to be emitted from portions of the screen which are contacted with the excitation beam as the drum is rotated, and an emission collecting system for collecting the energy emitted from the screen; an optics driver for moving the image acquisition optical system in a direction parallel to the rotational axis of the drum as the drum is rotated; and a drum drive mechanism which causes the rotatable drum to rotate. The system may further include embedded software for controlling system functions. Functions which the software may perform include, but are not limited to: interfacing with the system operator in accepting patient data, providing system status information, automatic image processing and analysis, and presentation of exam results.

In one variation, the apparatus may further include a screen erasing mechanism for erasing the storage layer radiation screen. According to this variation, the apparatus is able to be reused without having to remove the screen between scans. The screen erasing mechanism may be positioned adjacent the rotatable drum and used to release any radiation energy remaining stored on the screen after the screen has been read.

The screen erasing mechanism may also be positioned within the image acquisition optical system and moved by a same mechanism as the image acquisition optical system. The screen erasing mechanism may be designed to erase the screen as the screen is rotated without having to move the screen erasing mechanism. The screen erasing mechanism may be designed to provide energy over a sufficiently large area that the screen may be erased without either the erasing mechanism or the screen being moved.

In another embodiment, an apparatus is provided for forming and reading a radiation image of an object which comprises: a platform adjacent to which may be placed an object of which a radiation image is to be taken; a rotatable platter; a storage layer radiation screen mounted adjacent a surface of the rotatable platter; an electromagnetic wave radiation source positioned relative to the storage layer radiation screen and the platform such that radiation from the electromagnetic wave radiation source which traverses the platform and the object adjacent the platform is absorbed by the storage layer radiation screen; an image acquisition optical system positioned adjacent the platter, the image acquisition optical system including an excitation system for directing an excitation beam in the direction of the drum, the excitation beam causing energy to be emitted from portions of the screen which are contacted with the excitation beam as the platter is rotated, and an emission collecting system for collecting the energy emitted from the screens; an optics driver for moving the image acquisition optical system in a direction radially relative to the rotational axis of the platter as the platter is rotated; and a platter drive mechanism which causes the rotatable platter to rotate.

In one variation of this embodiment, the apparatus may further include a screen erasing mechanism for erasing the storage layer radiation screen. According to this variation, the apparatus is able to be reused without having to remove the screen between scans. The screen erasing mechanism may be positioned adjacent the rotatable platter and used to release any radiation energy remaining stored on the screen after the screen has been read. The screen erasing mechanism may optionally be contained within a screen erasing module which moves in a direction along the radius of the rotatable platter simultaneously with the rotation of the platter. The screen erasing mechanism may also be positioned within the image acquisition optical system and moved by a same mechanism as the image acquisition optical system. The screen erasing mechanism may be designed to erase the screen as the screen is rotated without having to move the screen erasing mechanism. The screen erasing mechanism may be designed to provide energy over a sufficiently large area that the screen may be erased without either the erasing mechanism or the screen being moved.

In another embodiment, an apparatus is provided which comprises: a storage layer radiation screen; an electromagnetic wave radiation source positioned relative to the storage layer radiation screen such that radiation from the electromagnetic wave radiation source which traverses an object adjacent the storage layer radiation screen is absorbed by the storage layer radiation screen; an image acquisition optical system including an excitation system for directing an excitation beam to the screen to cause energy to be emitted from portions of the screen which are contacted with the excitation beam, and an emission collecting system for collecting the energy emitted from the screen; and computer executable logic which is capable of taking data corresponding to energy emitted from the screen and signals corresponding to a reference image, normalizing the data corresponding to energy emitted from the screen relative to the reference image, and computing bone mineral density based on the normalized data.

According to this embodiment, data corresponding to energy emitted from the screen may be normalized relative to the reference image pixel by pixel. Also according to this embodiment, the storage layer radiation screen may have a non-planar surface, the computer executable logic further comprising logic for correcting for geometric distortion arising from the screen having a non-planar surface. The computer executable logic may compute bone mineral density based on a ratio between absorption in a bone region and absorption in a soft tissue region. The computer executable logic may also compute bone mineral density based on the equation $$BMD = \frac{1}{n} \Delta x \Delta y \sum_{i=1}^{n} \ln \frac{I_{wi}}{I_{(b+w)i}}$$

where $I_{wi}$ is absorption in the soft tissue region of the image;

$I_{(b+w)i}$ is absorption in the bone region which includes soft tissue.

In another embodiment, the apparatus comprises: a storage layer radiation screen having a non-planar surface; an electromagnetic wave radiation source positioned relative to the storage layer radiation screen such that radiation from the electromagnetic wave radiation source which traverses an object adjacent the storage layer radiation screen is absorbed by the storage layer radiation screen; an image acquisition optical system including an excitation system for directing an excitation beam to the screen to cause energy to be emitted from portions of the screen which are contacted with the excitation beam, and an emission collecting system for collecting the energy emitted from the screen; and computer executable logic which is capable of taking data corresponding to energy emitted from the screen and signals corresponding to a reference image, correcting for geometric distortion arising from the screen having a non-planar surface, and computing bone mineral density based on the corrected data. According to this embodiment, the storage layer radiation screen may be positioned on a rotatable cylindrically shaped rotatable drum.

The apparatuses of the present invention may be designed to operate as a single energy system and/or as a dual energy system. When designed to operate as a dual energy system, the electromagnetic wave radiation source is capable of emitting photons at two different energy levels. Alternatively, the apparatus may include a mechanism for altering an amount of energy delivered to the storage layer radiation screen.

According to any of the above apparatus embodiments, an object plate may be positioned adjacent the platform. The object plate may comprise an optically opaque but electromagnetic wave energy transmissive material. The object plate may include guides for the middle three fingers of a patient's hand.

The object plate may optionally be removable from the platform.

The object plate may optionally further include a hard tissue reference, such as a linear wedge of a material with energy absorption characteristics similar to those of human bone. A preferred material for the wedge is aluminum.

Several methods are also provided for forming and reading a radiation image of an object. In one embodiment, the method comprises: placing an object of which a radiation image is to be taken adjacent a platform that is positioned between a storage layer radiation screen and an electromagnetic wave radiation source such that radiation from the electromagnetic wave radiation source which traverses the object is absorbed by the storage layer radiation screen; forming a latent radiation image of the object on the storage layer radiation screen by causing the electromagnetic wave radiation source to emit radiation, a portion of the emitted radiation traversing the object and being absorbed by the storage layer radiation screen; and reading the latent radiation image of the object from the storage layer radiation screen.

According to one variation of the method, the storage layer radiation screen is mounted on a cylindrically shaped rotatable drum, reading the latent radiation image of the object from the storage layer radiation screen including causing energy to be emitted from portions of the screen which are contacted with an excitation beam as the drum is rotated, and collecting the energy emitted from the screen.

When the screen is positioned on the cylindrically shaped rotatable drum, it is noted that the image formed on the drum is distorted due to the fact that the screen is curved adjacent a curved surface of the drum. The method may further include correcting for distortion in the read latent radiation image due to the curvature of the screen adjacent the curved surface of the drum.

According to another variation of the method, the storage layer radiation screen is mounted on a rotatable platter, reading the latent radiation image of the object from the storage layer radiation screen including causing energy to be emitted from portions of the screen which are contacted with an excitation beam as the rotatable platter is rotated, and collecting the energy emitted from the screen. According to this variation, reading the latent radiation image may include moving an image acquisition optical system radially as the rotatable platter is rotated.

In another embodiment, the method comprises: placing an object of which a radiation image is to be taken between a storage layer radiation screen and an electromagnetic wave radiation source such that radiation from the electromagnetic wave radiation source which traverses the object is absorbed by the storage layer radiation screen; forming a latent radiation image of the object on the storage layer radiation screen by causing the electromagnetic wave radiation source to emit radiation, a portion of the emitted radiation traversing the object and being absorbed by the storage layer radiation screen; reading the latent radiation image of the object from the storage layer radiation screen; and normalizing the latent radiation image using a reference image. Normalizing the latent radiation image may include normalizing each pixel of the latent radiation image relative to a corresponding pixel on the reference image. The method may further include calculating bone mineral density from the normalized latent radiation image. Computing bone mineral density may be based on a ratio between absorption in a bone region and absorption in a soft tissue region and may be based on the equation $$BMD = \frac{1}{n}\Delta x \Delta y \sum_{i=1}^{n} \ln \frac{I_{wi}}{I_{(b+w)i}}$$

where
$I_{wi}$ is absorption in the soft tissue region of the image;
$I_{(b+w)i}$ is absorption in the bone region which includes soft tissue.

In yet another embodiment, a method for forming and reading a radiation image of an object, the method comprising: placing an object of which a radiation image is to be taken between a storage layer radiation screen having a non-planar surface and an electromagnetic wave radiation source such that radiation from the electromagnetic wave radiation source which traverses the object is absorbed by the storage layer radiation screen; forming a latent radiation image of the object on the storage layer radiation screen by causing the electromagnetic wave radiation source to emit radiation, a portion of the emitted radiation traversing the object and being absorbed by the storage layer radiation screen; reading the latent radiation image of the object from the storage layer radiation screen; and correcting for geometric distortion arising from the screen having a non-planar surface. According to the method, normalizing the latent radiation image may include normalizing each pixel of the latent radiation image relative to a corresponding pixel on the reference image. The method may further include calculating bone mineral density from the normalized latent radiation image.

According to the above method embodiments, the storage layer radiation screen is preferably stationary relative during the formation of the latent radiation image.

According to the above apparatuses and methods, the object may be any part of the body for which bone mineral density is to be measured. Examples of body parts that may be read include, but are not limited to a part of an arm or leg, preferably a part of a hand or foot, more preferably a wrist, fingers and/or toes. In one particular embodiment, the part of the body includes the middle three fingers of a person's hand.

In regard to each of the above embodiments, the platform may include a hard tissue reference, such as a linear wedge of a material with electromagnetic wave radiation absorption characteristics similar to those of human bone. In a preferred embodiment, the hard tissue reference is made of aluminum. The hard tissue reference preferably has a known thickness profile which may be used to calibrate the system.

It is noted that while a reference object may be included in or used with the system for the purpose of a diagnostic of the x-ray source, the system of the present invention are designed such that the reference object is not required.

In a preferred embodiment, a plurality of different systems are tested using a set of known test objects in order to calibrate the gain and offset for each of the plurality of different systems so that inter-system variability is reduced. By doing inter-system calibration, the need for a reference object is reduced.

Because of variations in x-ray intensity across the x-ray exposure field, and/or the presence of fixed defects in the storage layer radiation screen, the methods of the present invention may further include using a reference image taken when no external object is present on the hand support plate and using the reference image to correct the read latent radiation image. The reference image serves to normalize each pixel of the storage radiation screen so that different readings of latent radiation images may be accurately compared. In a preferred embodiment, the reference image is stored in memory and used with a series of read latent radiation images. Alternatively, a reference image may be taken for each read latent radiation image.

BRIEF DESCRIPTION OF THE FIGURES

FIG. 5A illustrates the screen scanning system mounted on the base panel.

FIG. 5B illustrates the image processing system mounted on the rear panel and connected to the image acquisition system.

FIG. 5C illustrates the top panel of the apparatus including the electromagnetic wave source and an interactive display panel.

FIG. 5D illustrates the throat panel forming a platform and containing an object plate.

FIG. 5E illustrates an object plate used with the apparatus.

FIG. 5F illustrates a patient's hand positioned on the object plate prior to an electromagnetic wave radiation exposure.

FIGS. 8A–8M provide a sequence of graphical user interfaces which illustrate an embodiment of session in which bone mineral density is determined using the apparatus of the present invention.

FIG. 8A illustrates a user interface which may be displayed prior to a user logging on to the apparatus.

FIG. 8B illustrates a user interface which may be shown during autocalibration of the instrument.

FIG. 8C illustrates a user interface which shows some of the options available to the user for the operation of the instrument.

FIG. 8D illustrates a user interface which may be displayed when a new examination is ready to be conducted.

FIG. 8E illustrates a user interface which allows the operator to review and modify patient data after it has been entered.

FIG. 8F illustrates a user interface which provides an instruction and visual guide regarding how to properly position a patient's hand for x-ray exposure.

FIG. 8G illustrates a user interface which indicates that an exposure is being taken.

FIG. 8H illustrates a user interface indicating that the exposure is complete and directs the operator to remove the patient's hand from the apparatus.

FIG. 8I illustrates a user interface that may be displayed once the image has been read.

FIG. 8J illustrates a user interface which allows a operator to select the portion of the image on which to perform the analysis.

FIG. 8K illustrates a user interface which allows a operator to further select the portion of the image on which to perform a bone mineral density calculation.

FIG. 8L illustrates a user interface which allows a operator to adjust the position of a line transecting one of the fingers on which a scan is to be performed.

FIG. 8M illustrates a user interface which displays the final result of the bone mineral density scan.

DESCRIPTION OF THE PREFERRED EMBODIMENTS

Figure 1A:
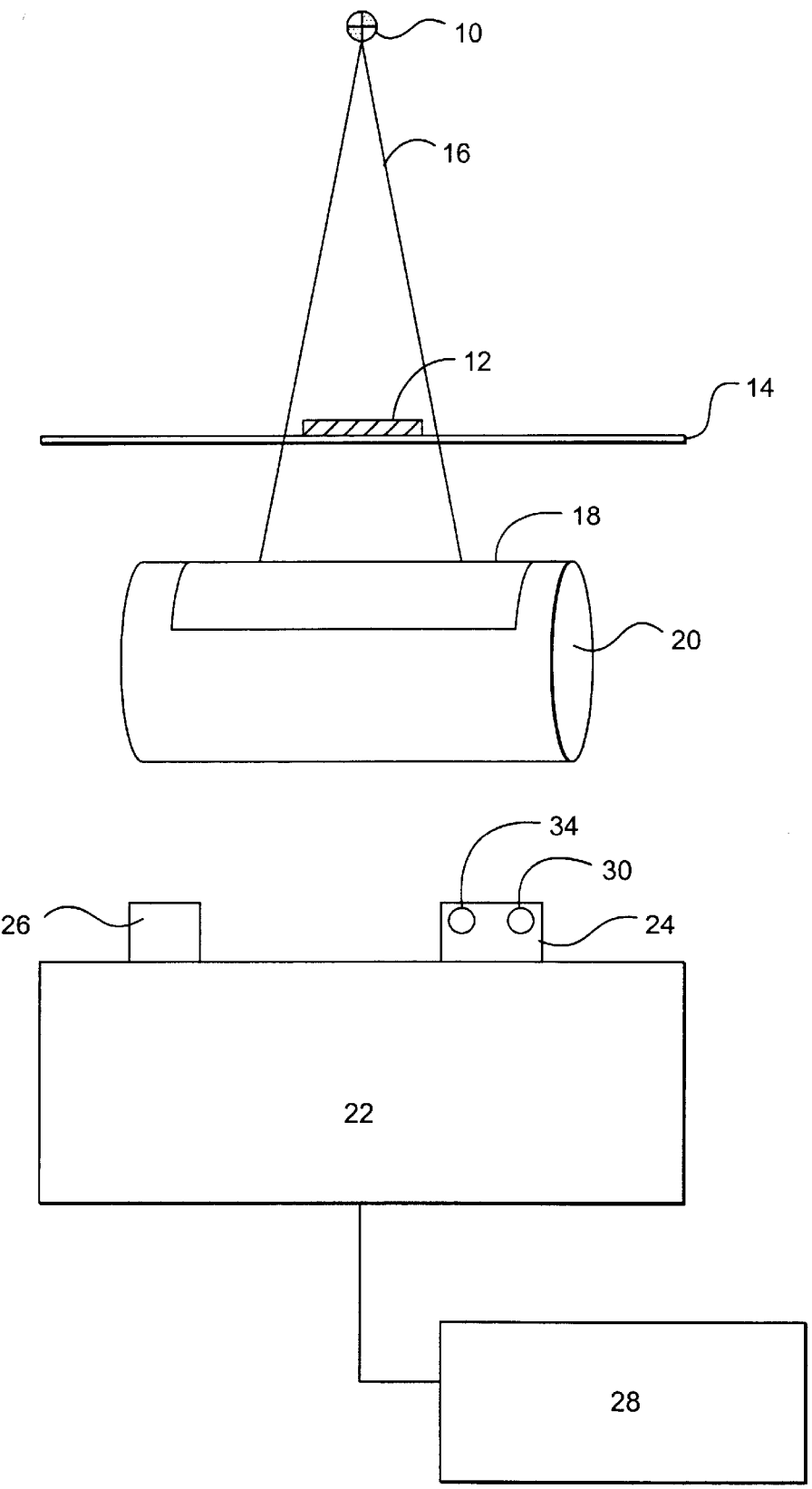
FIG. 1A illustrates the exposure of an object to electromagnetic wave radiation and the recording of an image of the object on a storage layer radiation screen which is mounted on a rotatable drum.
Figure 1B:
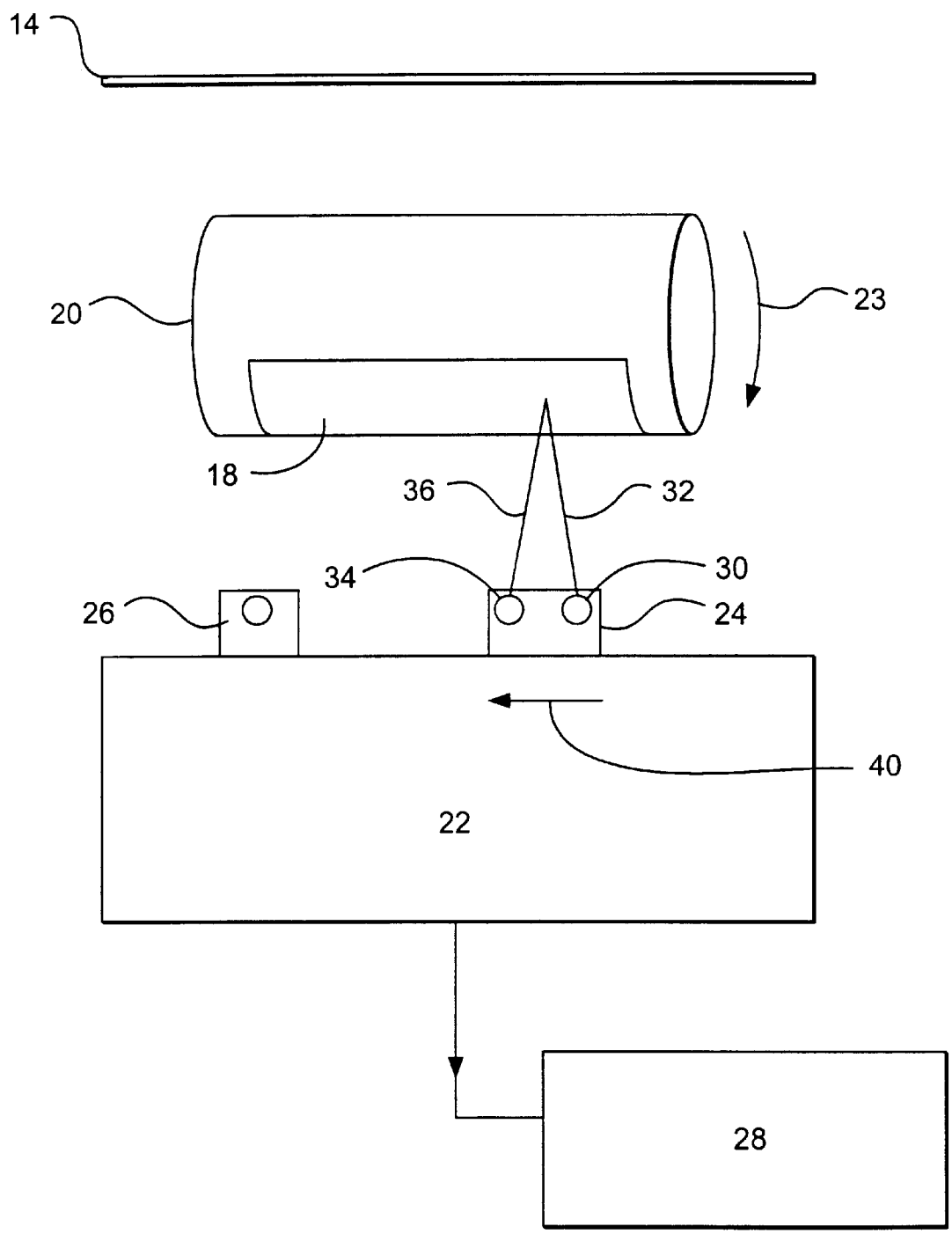
FIG. 1B illustrates the reading of the image stored on the storage layer screen by an image acquisition system.
Figure 1C:
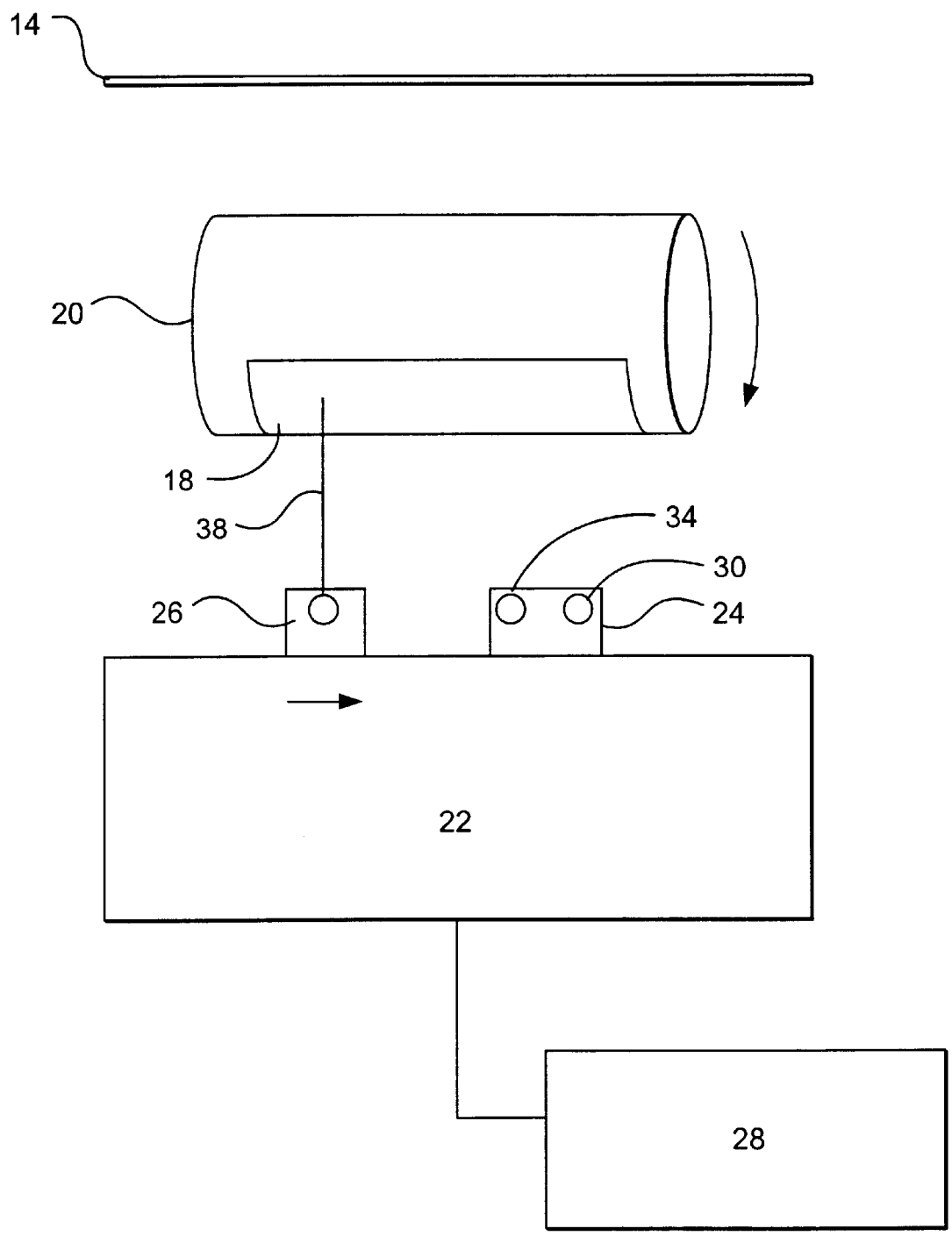
FIG. 1C illustrates the erasure of a screen by a screen erasing mechanism after the screen has been read.

An embodiment of an apparatus according to the present invention which includes a rotatable drum, and its operation, is illustrated in FIGS. 1A–1C. As illustrated in the figures, the apparatus includes an electromagnetic wave radiation source 10 positioned above a platform 14. An object 12 to be analyzed may be placed on the platform 14 and exposed to electromagnetic wave radiation from the source 10. It is noted that the electromagnetic wave radiation source 10 is preferably stationary relative to the platform 14 and the underlying components.

The apparatus also includes a storage layer radiation screen 18 mounted on the cylindrically shaped rotatable drum 20 and a storage layer radiation screen 18 mounted on the drum. A rotation mechanism (not shown) causes and controls the rotation of the drum 20. The apparatus is designed so that the storage layer radiation screen 18 may be used over and over again without having to remove the screen from the apparatus, for example, to clean it, to form an image on it, or read it.

Also illustrated in the figures is an image acquisition optical system 24 which includes an illumination system 30 which provides an excitation beam 32 (shown in FIG. 1B) to excite an area of the screen 18. In response to the excitation beam 32, the screen emits energy 36 (shown in FIG. 1B) which is collected by an emission collecting system 34. The emission collecting system 34 generates signals which are used by an image processing system 28 to form a visible image of the latent radiation image. The image acquisition optical system 24 is attached to an optics driver 22 such that the image acquisition optical system 24 may be moved in a direction 40 parallel to the rotational axis of the rotating drum 20. Rotation of the drum 20 and the movement of the image acquisition optical system 24 relative to the drum 20 in a direction parallel to the drum's rotational axis may be performed by different motors or by a single motor.

The system further includes a screen erasing mechanism 26 which is positionable adjacent the rotatable drum 20 and is used to release any radiation energy remaining stored on the screen after the screen has been read. Once erased, the screen can be reused in a subsequent scan.

The object 12 used to form a radiation image may be any part of the body for which bone mineral density is to be measured. Typically, the part of the body is a part of an arm or leg, most typically part of a hand or foot. For example, the part of the body may include a wrist, foot, hand, fingers and/or toes. In one particular embodiment, the part of the body includes the middle three fingers of a person's hand.

The storage layer radiation screen may be any screen capable of forming a latent radiation image when exposed to electromagnetic wave radiation. In general, latent radiation images are created by exposing a storage radiation screen to a form of electromagnetic wave radiation, such as x-rays, α-rays, β-rays, γ-rays, cathode rays and ultraviolet rays. When the electromagnetic wave radiation is passed through an object onto the screen, the electromagnetic wave radiation forms a latent radiation image on the screen by exciting the phosphor crystals within the storage layer into a meta-stable condition. The storage layer may be formed of any compound which is excited into a meta-stable state when it absorbs electromagnetic wave radiation such as x-rays, α-rays, β-rays, γ-rays, cathode rays and ultraviolet rays, and which, when stimulated by suitable electromagnetic wave radiation, emits electromagnetic wave radiation of a different frequency.

The storage layer is preferably a storage luminophore and is most preferably a stimulable phosphor. The phospholuminescent material converts incoming electromagnetic wave radiation to light, which increases the detection efficiency of the sensor. The stimulable phosphor is preferably stimulated by light having a wavelength between about 590 and 700 nm. The stimulable phosphor also preferably emits light energy at a wavelength greater than 300 nm, more preferably greater than 390 nm. The stimulable phosphor is also preferably stimulated by light having a wavelength at least 50 nm larger than light emitted from the storage layer. Examples of suitable phospholuminescent materials include bariumbromo halides doped with europium ions (BaBrX:Eu+2), where X may any combination of variety of halides including fluorine, chlorine, or iodine. A variety of storage layer radiation screens have been developed, including screens made by Fuji, Kodak and AGFA, any of which may be used in this invention.

FIG. 1A illustrates a first stage of operation of the apparatus. As illustrated, electromagnetic wave radiation 16 emanating from the electromagnetic wave radiation source 10 passes through the object 12 and forms a latent radiation image on the storage layer radiation screen 18 mounted on the cylindrically shaped rotatable drum 20. The drum 20 is stationary when the electromagnetic wave radiation 16 is delivered.

FIG. 1B illustrates the operation of the screen scanning system during which time the latent radiation image of the object 12 is read. As illustrated, the image acquisition optical system 24 reads the latent radiation image recorded on the storage layer screen 18 as the screen is rotated 23 past the image acquisition optical system 24. In general, the image is read by scanning the screen using a suitable electromagnetic wave radiation, such as visible light or infrared rays (hereinafter referred to as "stimulating rays"), which causes the radiation energy stored in the storage layer to be released as a light emission. The light emitted from the storage layer is then detected and converted into data corresponding to the image.

As illustrated in FIG. 1B, the image acquisition optical system 24 is positioned adjacent the rotatable drum 20 and is moveable parallel to the rotational axis of the drum 20. The image acquisition optical system 24 is attached to an optics driver 22 such that the image acquisition optical system 24 may be moved in a direction 40 parallel to the rotational axis of the rotating drum 20. Rotation of the drum 20 and the movement of the image acquisition optical system 24 relative to the drum 20 in a direction parallel to the drum's rotational axis may be performed by different motors or by a single motor.

During operation of the screen scanning system, the drum 20 is preferably rotated at a speed of at least 60 revolutions per minute, more preferably at least 300 revolutions per minute. In general, the rate at which the drum is rotated is dependent on the size of the pixels forming the image being read, the size of the pixels depending on the quality of the storage layer used in the screen and the resolution being sought to be achieved. It is preferable to rotate the drum at higher rates in order to enable the screens to be scanned at faster rates.

As the screen 18 passes the image acquisition optical system 24 during each revolution of the drum 20, a different line-shaped portion of the screen 18 is read, the width of the line corresponding to the width of a pixel. The acquisition optical system 24 preferably reads pixels having a width between about 30 and 200 microns. As the drum 20 is rotated, the image acquisition optical system 34 is simultaneously moved in a direction 40 parallel to the axis of rotation of the drum 20 such that a new line-shaped portion of screen 18 is read during each revolution of the drum 20. By moving the image acquisition optical system 24 at an appropriate speed, the image acquisition optical system 24 can be scanned over different narrow line-shaped areas of the screen, thereby enabling the entire surface area of the screen to be scanned. For example, in order to generate an image having a pixel size of 40 microns, the drum 20 may be rotated at 342 revolutions per minute while the image acquisition optical system 24 is moved simultaneously in a direction 40 parallel to the axis of rotation of the drum 20 at a rate of about 241 microns per second.

As the drum 20 rotates, the illumination system 30 of the image acquisition optical system 24 provides an excitation beam 32 to excite an area of the screen 18. In response to the excitation beam 32, the screen emits energy 36 which is collected by the emission collecting system 34. In one variation, the emission collecting system 34 includes a photodetector (not shown) which records light which reaches the photodector as electrical signals. The electrical signals are conveyed to the image processing system 28 and are used by the image processing system 28 to form a visible image of the latent radiation image.

The system of the present invention may be operated as a single energy system and/or as a dual energy system. When operated as a single energy system, the system performs a single scan at one energy level. When the system is operated as a dual energy system, the system may perform a first scan where the electromagnetic wave radiation source provides energy at a first energy level and then performs a second scan where the electromagnetic wave radiation source provides energy at a second, different energy level. For example, a first image is generated at a first energy level and is read off the storage layer screen 18 by the image acquisition optical system 24. Then, a second image is generated at a second, different energy level and is read off the storage layer screen 18 by the image acquisition optical system 24. The first and second energy level images may be displayed for verification by an operator. Once acceptable images are obtained, the dual energy images may be processed using known techniques to determine the patient's bone mineral density.

In a preferred embodiment, the electromagnetic wave radiation is an x-ray source, which may be a radionuclide capable of emitting photons at two different energy levels. One possible radionuclide source is gadolinium-153 which can emit x-rays at a lower energy of 44 kV and an upper energy of 100 kV. An electromagnetic x-ray filter is removably positioned between the object and the source to filter out all the low energy emission. One filter for use with gadolinium-153 and capable of blocking all 44 kV emission, is made of copper. A preferred embodiment for the x-ray source is an electrically controlled source, capable of switching kilovoltage between high and low energies, with a metallic k-edge filter interposed in the x-ray beam during the high energy exposure.

After the screen has been read, a screen erasing mechanism 26 is employed to release any energy which remains stored on the screen 18. Once erased, the screen can be used again to form a new latent radiation image. The screen erasing mechanism 26 is positioned or positionable sufficiently adjacent the rotatable drum 20 that the energy provided by the screen erasing mechanism 26 can release any energy remaining stored on the screen after the screen has been read. Erasure of the screen allows the screen to be used over and over again. Incorporation of the screen erasing mechanism 26 within the system avoids the screen having to be removed between scans in order to be erased. By avoiding the need to remove the screen, there is no need to handle or clean the screen, thereby reducing the amount of defects formed in the screen due to handling, increasing the useful life of the screen and the apparatus, and reducing the amount of maintenance which needs to be performed on the apparatus.

The screen erasing mechanism may include a high intensity light source which provides erasing light at a wavelength suitable for exciting the storage layer to cause the emission of any radiation energy stored on the screen after the entire screen has been read. The erasing light preferably emits light comprising light having the same wavelength as the excitation beam.

In FIGS. 1A–1C, the screen erasing mechanism 26 is illustrated as being coupled to the optics driver 22 and separate from the image acquisition optical system 24. In this embodiment, the screen erasing mechanism 26 may be moved in a direction 42 parallel to the drum's rotational axis by the optics driver 22 or by a separate drive mechanism.

Figure 1D:
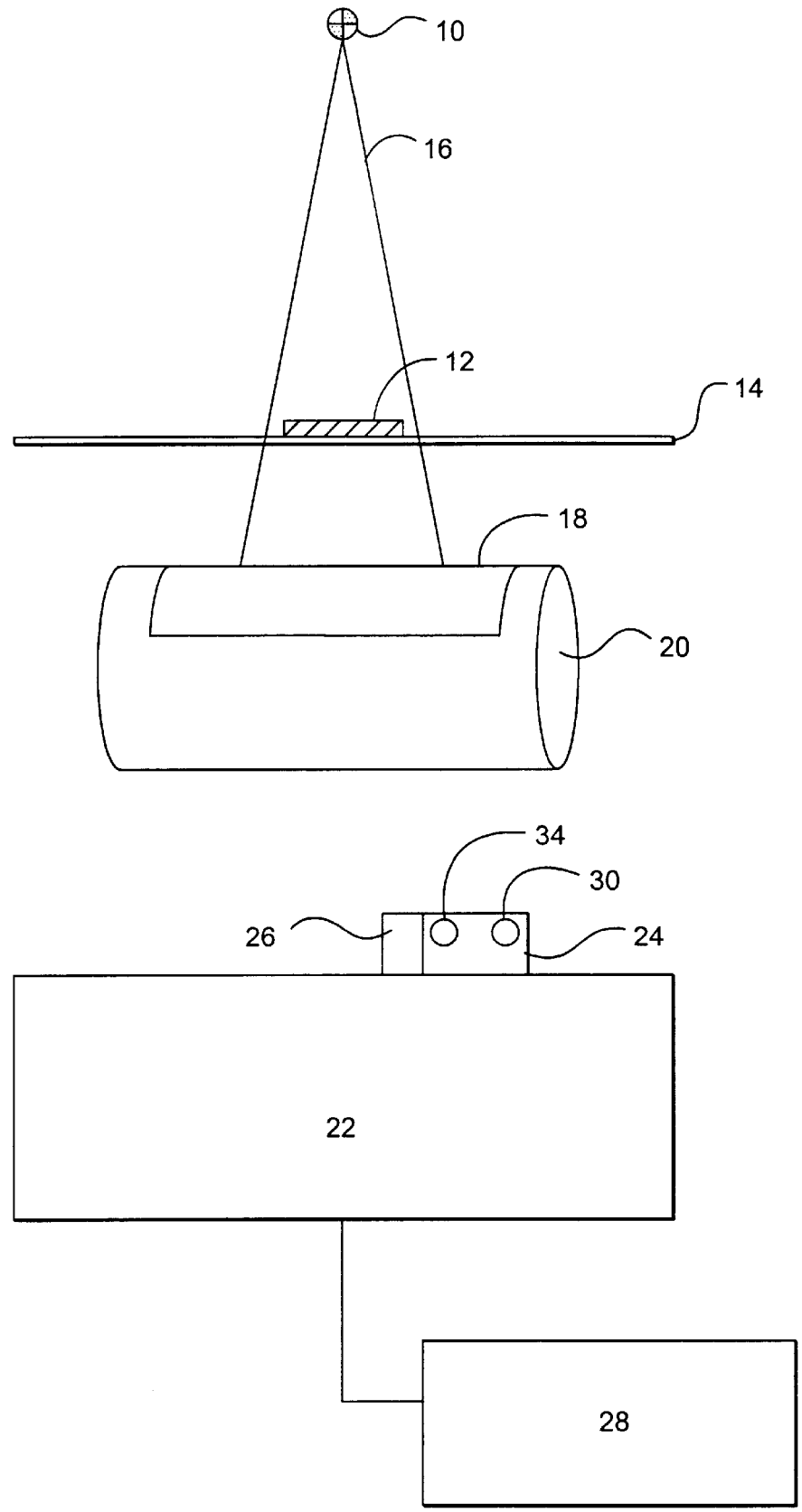
FIG. 1D illustrates an alternate embodiment of the screen erasing mechanism where the screen erasing mechanism is positioned within the image acquisition optical system.

Alternatively, as illustrated in FIG. 1D, the screen erasing mechanism may be positioned within or coupled to the image acquisition optical system 24, thereby allowing the screen erasing mechanism to be moved by the same mechanism as the image acquisition optical system 24. In this variation, the image acquisition optical system 24 operates during a scan where the optics driver 22 moves the image acquisition optical system 24 as the drum is rotated. During an erasure, the screen erasing mechanism 26 is operating and the image acquisition optical system 24 is off as the optics driver 22 moves the image acquisition optical system 24.

Figure 1E:
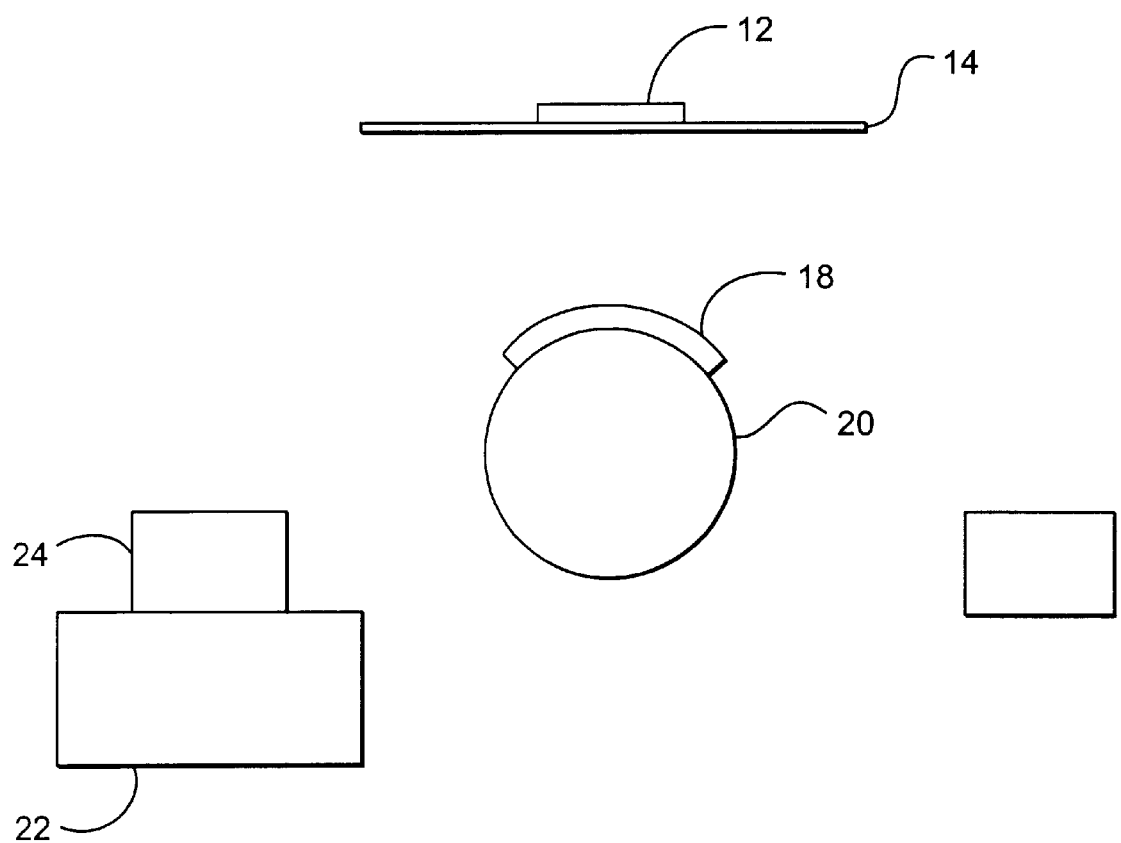
FIG. 1E illustrates an alternate embodiment of the screen erasing mechanism where the screen erasing mechanism is positioned separate from the optics driver.

As illustrated in FIG. 1E, the screen erasing mechanism 26 may optionally be positioned separate from the optics driver 22 and may be moved by another mechanism. FIG. 1E illustrates a side view of the apparatus where the electromagnetic wave radiation source 10, the image acquisition optical system 24, and the screen erasing mechanism 26 are positioned in a triangle around the drum 20.

It is noted that the screen erasing mechanism 26 may also be stationary relative to the drum 20 so long as it provides sufficient illumination to erase the screen 18.

Depending on the design of the screen erasing mechanism 26, the drum may be either rotated or stationary during erasure. For example, in regard to FIG. 1E, the drum may be oriented when an image is being formed such that the screen 18 is positioned facing the electromagnetic wave radiation source 10 and may be oriented when the screen is being erased such that the screen 18 is positioned facing the screen erasing mechanism 26, so long as the screen erasing mechanism 26 provides sufficient illumination to erase the screen 18.

Figure 2A:
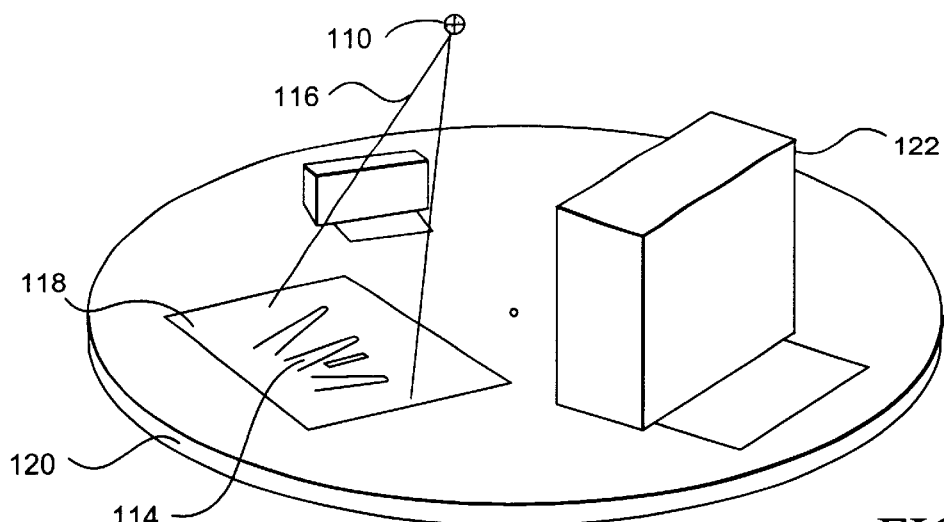
FIG. 2A illustrates the exposure of an object to electromagnetic wave radiation and the recording of an image of the object on a storage layer radiation screen which is mounted on a rotatable platter.
Figure 2B:
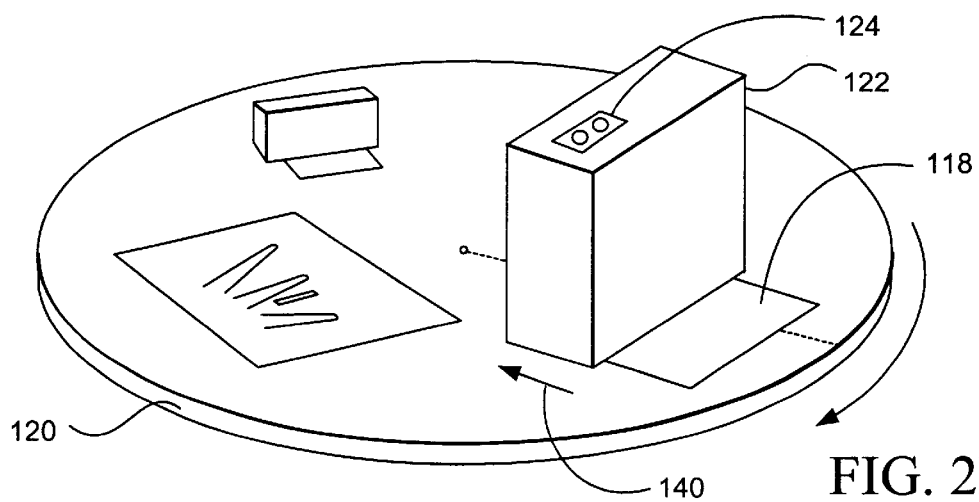
FIG. 2B illustrates the reading of the image stored on the storage layer screen by an image acquisition system.
Figure 2C:
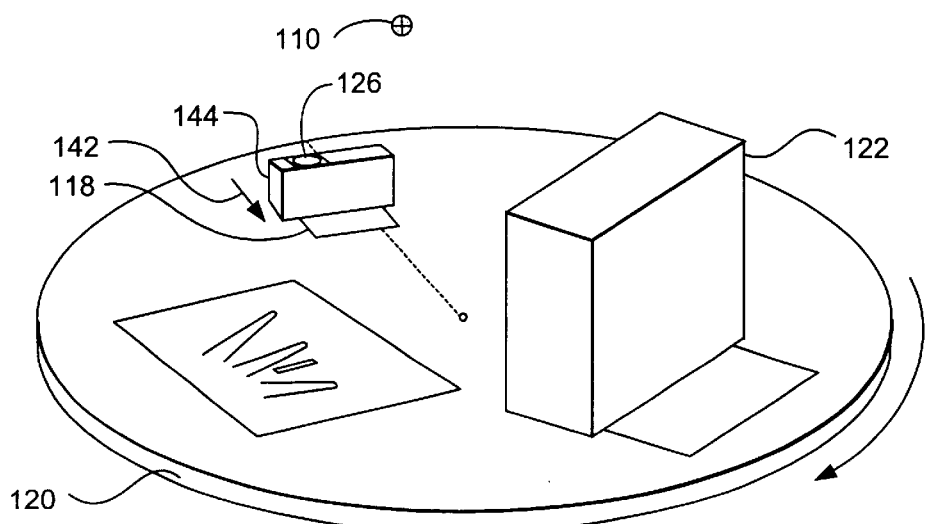
FIG. 2C illustrates the erasure of a screen by a screen erasing mechanism after the screen has been read.

FIGS. 2A–2C illustrate an alternate embodiment of the present invention which includes a rotatable platter instead of a rotatable drum as the screen holder. As illustrated in FIGS. 2A–2C, the storage layer radiation screen 118 is mounted on a rotatable platter 120. An electromagnetic wave radiation source 110 is positioned above a platform 114 onto which an object to be imaged may be placed. The electromagnetic wave radiation source 110 is preferably stationary relative to the platform 114 and the underlying components.

The rotatable platter 120 is positioned between the platform 114 and the electromagnetic wave radiation source 110. As a result, when electromagnetic wave radiation is delivered from the electromagnetic wave radiation source 110, electromagnetic wave radiation which traverses the platform 114 and the object is absorbed by the storage layer radiation screen 118 mounted on the rotatable platter 120.

The system further includes an image acquisition optical system 124. The image acquisition optical system 124 is contained within an optics module 122 such that the image acquisition optical system 124 may be moved in a direction 140 along a radius of the rotatable platter 120. The system also includes a screen erasing mechanism 126 for releasing any radiation energy remaining on the screen after the screen is read. The screen erasing mechanism 126 is illustrated as being separate from the optics module 122 but may be incorporated into the optics module. In general, the screen erasing mechanism 126 may be modified as described above regarding FIGS. 1C–1E.

FIG. 2A illustrates the exposure and recording of an electromagnetic wave radiation image of an object according to this embodiment. As illustrated, electromagnetic wave radiation 116 is delivered from the electromagnetic wave radiation source 110. A portion of the radiation passes through the object plate 114 and an object positioned thereon and is absorbed by the storage layer radiation screen 118 mounted on the rotatable platter 120. The storage layer radiation screen 118 is stationary as the electromagnetic wave radiation 116 is delivered.

As noted above, the object may be any part of the body for which bone mineral density is to be measured. Typically, the part of the body is a part of an arm or leg, most typically part of a hand or foot. For example, the part of the body may include a wrist, foot, hand, fingers and/or toes. In one particular embodiment, the part of the body includes the middle three fingers of a person's hand.

FIG. 2B illustrates the operation of the screen scanning system according to this embodiment. As illustrated in FIG. 2B, the rotatable platter 120 is rotated during the screen scanning and the image acquisition optical system 124 reads the image stored on the storage layer screen 118 as the screen is rotated past the image acquisition optical system 124. The image acquisition optical system 124 is contained within an optics module 122 such that the image acquisition optical system 124 may be moved in a direction 140 along a radius of the rotating platter 120. By moving the image acquisition optical system 124 radially as the platter 120 is rotated, the image acquisition optical system 124 reads a spiral line of pixels which together form the image.

As illustrated in FIG. 2C, the screen erasing mechanism 126 may be contained within a screen erasing module 144 which can move in a direction 142 along the radius of the rotatable platter 120 simultaneously with the rotation of the platter 120. In an alternate embodiment, the screen erasing mechanism may be positioned within the image acquisition optical system 124, thereby allowing the screen erasing mechanism to be moved by the same mechanism as the image acquisition optical system 124. Alternatively, the screen erasing mechanism 126 may be designed such that it can erase the screen as the screen is rotated without having to move the screen erasing mechanism 126. Alternatively, the screen erasing mechanism 126 may provide energy over a sufficiently large area that the screen may be erased without either the erasing mechanism or the screen being moved. When the screen has been erased, a new image may be recorded on the screen.

Figure 2D:
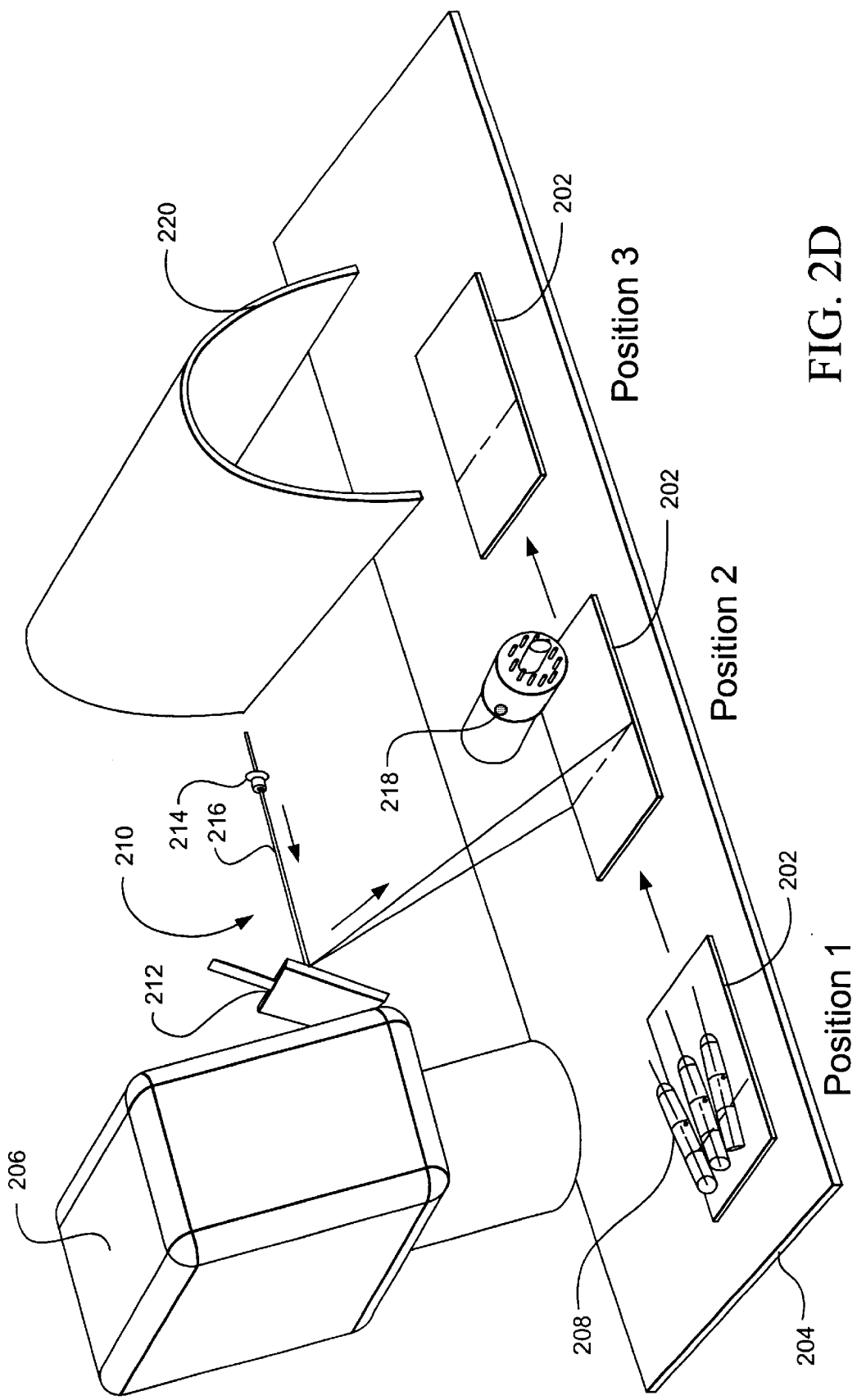
FIG. 2D illustrates an embodiment of the present invention which includes a platform with a laterally moveable screen instead of a rotatable drum or a rotatable platter as the screen holder.

FIG. 2D illustrates an alternate embodiment of the present invention which includes a platform with a laterally moveable screen instead of a rotatable drum or a rotatable platter as the screen holder. As illustrated in FIG. 2D, the storage layer radiation screen 202 is mounted on a platform 204 which allows the screen 202 to be moved as indicated by the arrows between a screen exposure position (Position 1), a screen reading position (Position 2), and a screen erasing position (Position 3). Situated over the screen exposure position of the platform is an electromagnetic wave radiation source 206. As illustrated, an object 208 to be imaged may be placed between the electromagnetic wave radiation source 206 and the screen 202. The electromagnetic wave radiation source 206 is preferably stationary relative to the platform 204. When electromagnetic wave radiation is delivered from the electromagnetic wave radiation source 206, electromagnetic wave radiation which traverses the object 208 is absorbed by the storage layer radiation screen 202 mounted on the platform 204.

The system further includes an image acquisition optical system 210. In the embodiment that is illustrated, the image acquisition optical system 210 includes a galvonometer 212 or other suitable mechanism for scanning a laser beam, a laser 214 (shown as a laser diode) which directs a laser beam 216 off the galvonometer 212 to a storage layer radiation screen 202 which has been moved to the screen reading position (Position 2), and a detector (PMT tube) 218 which collects radiation emitted from the storage layer radiation screen 202 in response to the laser energy directed to the storage layer radiation screen 202.

The system also includes a screen erasing mechanism 220, illustrated as an eraser/reflector which is used to release any radiation energy remaining on the screen after the screen is read. The screen erasing mechanism 220 is positioned over the screen erasing position (Position 3) of the platform. After the screen 202 is erased in Position 3, the screen 202 is returned to Position 1 so that a new image may be formed on the screen 202.

It is noted that the systems described in regard to FIGS. 2A–2D can be designed to operate as a single energy system or a dual energy system as described above in regard to FIGS. 1A–1C. When operated as a single energy system, the system performs a single scan at one energy level. When the system is operated as a dual energy system, the system may perform a first scan where the electromagnetic wave radiation source provides energy at a first energy level and then performs a second scan where the electromagnetic wave radiation source provides energy at a second, different energy level.

In regard to the systems shown in FIGS. 1A–1C and FIGS. 2A–2D, the object plate may optionally include a hard tissue reference, such as a linear wedge of a material with electromagnetic wave radiation absorption characteristics similar to those of human bone.

Figure 3:
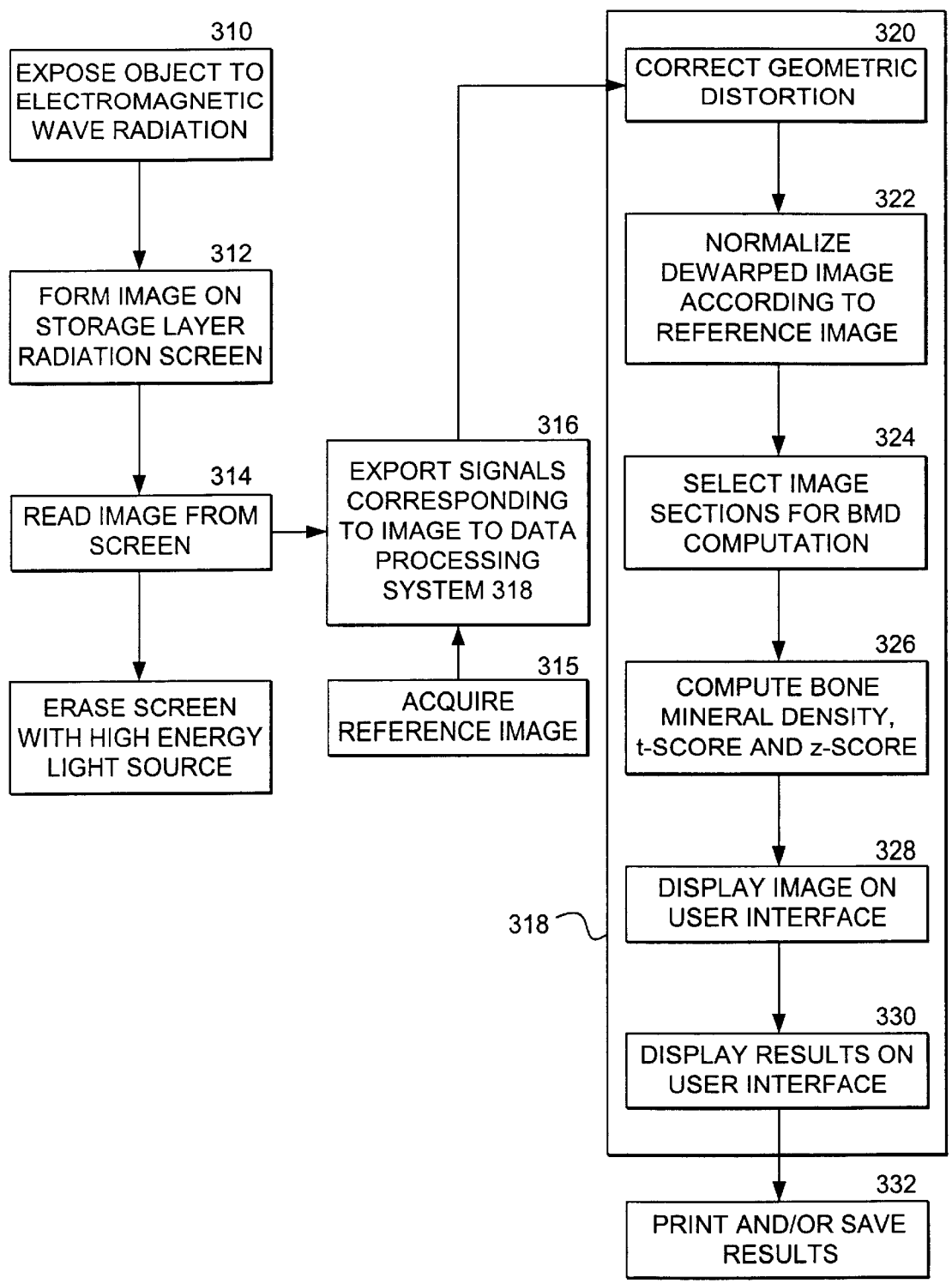
FIG. 3 illustrates a process flow sequence used in performing the imaging method of the present invention.

FIG. 3 illustrates a sequence of steps which may be used to compute bone mineral density according to the present invention. In step 310, a portion of a patient's body, for example the patient's hand, is exposed to electromagnetic wave radiation (e.g., x-ray irradiation). As a result, in step 312, a latent radiation image of the object is formed on a storage layer radiation screen which is mounted on a drum or a rotatable platter of the apparatus. In step 314, the image is read. This may be done by rotating the storage layer screen containing the latent radiation image while the image acquisition system moves relative to the screen. As discussed above, reading of the image is accomplished by an image acquisition system which illuminates portions of the screen with an excitation beam and detects energy emitted from the illuminated storage layer screen. The emitted radiation is detected by a photodetector in the image acquisition system and converted to signals. In step 316, the signals are communicated to a data processing system 318. In step 330, the screen is erased by causing any energy which remains stored on the screen to be released. Erasure can be done sequentially or concurrently with data processing the image.

In step 315, a reference image is acquired. The reference image can be taken before or after an image of an object is taken. The signals corresponding to the reference image are also communicated to the data processing system 318. The reference image is an image that is taken when no external object is present. This allows the system to determine a baseline for each pixel of the storage layer radiation screen. As discussed herein, the baseline for pixels can vary due to variations in x-ray intensity across the x-ray exposure field, and/or the presence of fixed defects in the storage layer radiation screen. The reference image serves to normalize each pixel of the storage radiation screen so that different readings of latent radiation images may be accurately compared. By combining the data for the reference image and the image of the object, a normalized image is obtained.

The data processing system 318 analyzes the signals produced during step 316 in combination with the reference image in order to calculate bone mineral density. In step 320, the system corrects for geometric distortion. This correction is required when the storage layer radiation screen is positioned on a curved surface, such as a cylindrical drum.

In step 322, the corrected (dewarped) image is normalized using data corresponding to the reference image.

In step 324, the data processing system selects sections of the normalized image on which to perform BMD computations. The operator may select non-anomalous sections of the image on the user interface for computation of bone mineral density. Alternatively, step 324 may be performed by the apparatus without operator intervention.

In step 326, the data processing system computes bone mineral density, t-scores and z-scores and any other necessary analysis of the image for the selected sections.

In step 328, the image may be displayed to the user on a user interface.

In step 330, the results are displayed on a user interface.

In step 332, the data processing system 318 may store the results of the scan and the analysis and/or print the results of the scan and the analysis, and/or perform any further processes which may be needed.

It is noted that the data processing system 318 may be attached to a variety of instruments including a memory device, a printer, a server. Results may be saved locally or remotely. Results may also be printed locally or remotely. For example, the results may be transmitted over an internal or external network.

Figure 4:
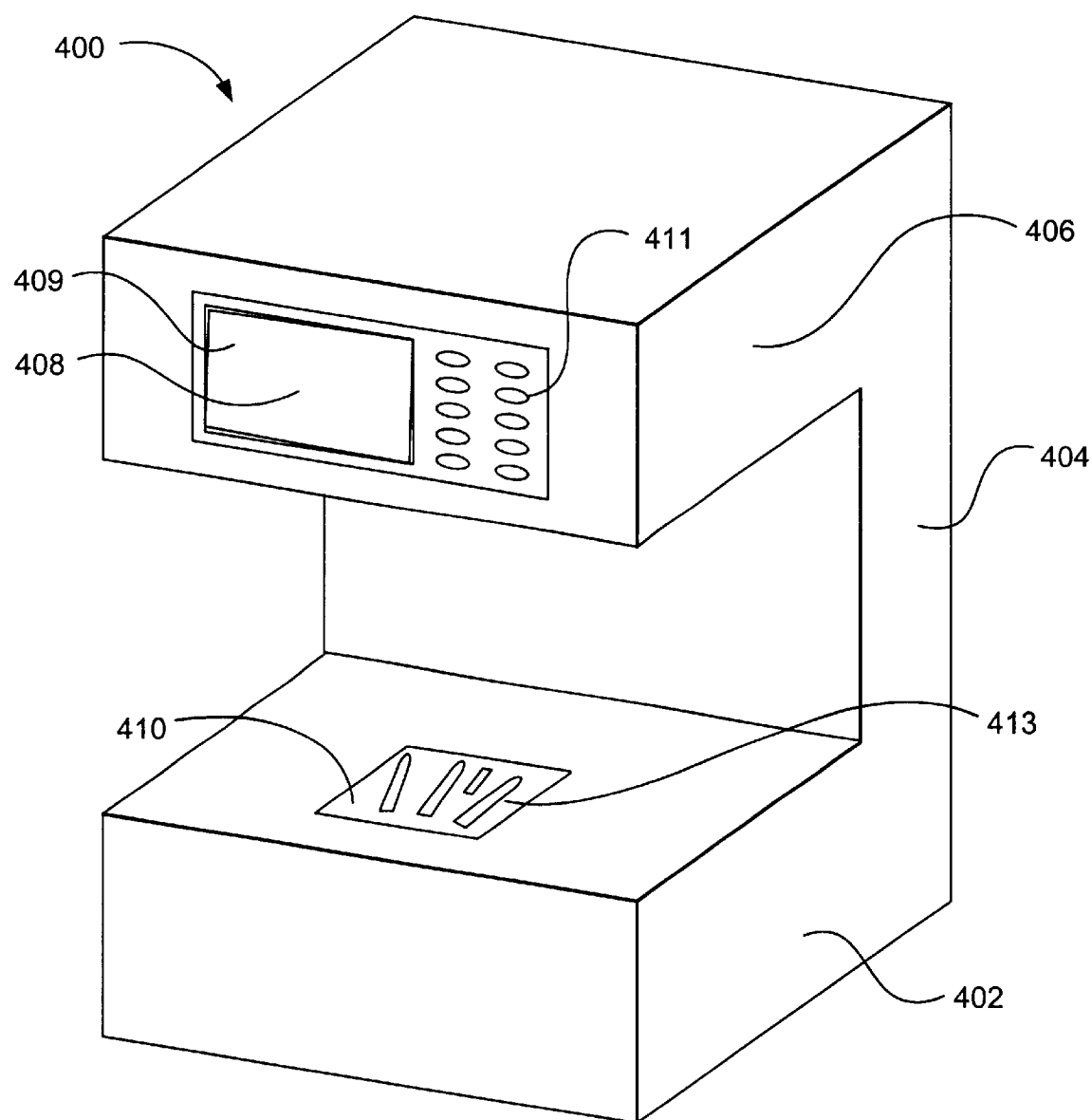
FIG. 4 illustrates a housing for an apparatus according to the present invention.

FIG. 4 illustrates an external housing 400 which may be used with either the apparatus illustrated in FIGS. 1A–1C or the apparatus illustrated in FIGS. 2A–2C. The base 402 of the housing includes the rotatable drum (FIGS. 1A–1C) or rotatable platter (FIGS. 2A–2C) on which is mounted a storage layer radiation screen. The base 402 also includes the image acquisition optical system and the erasing mechanism. As can be seen from the layouts of the apparatuses of FIGS. 1–2, the base needs to be higher when a rotatable drum is employed and needs to be deeper when a rotatable platter is employed.

A top 410 of the base 402 serves as the platform on which an object to be scanned may be positioned. As will be described herein, an object plate 413 which guides the positioning of the object relative to the platform and the energy source may be positioned on the top 410. A hard tissue reference 415 may also be placed on the top 410 of the base 402. The object plate 413 shown is designed to accommodate a patient's middle three fingers, but may be adjusted to accommodate larger structures such as the metacarpal or forearm.

The electromagnetic wave energy source is positioned within the top panel 406 such that electromagnetic wave energy from the source can be directed to the screen positioned in the base 402. Proper shielding of the electromagnetic wave energy to protect users is preferably built into the housing.

The data processing system may optionally be housed in the back panel 404 but can be positioned wherever space is available in the housing.

A user interface 408 including a display surface 409 and mechanisms 411 for inputting information and controlling the operation of the apparatus may be positioned on a surface of the top panel 406.

As can be seen from FIG. 4, the housing 400 has an open design which is convenient for allowing the patient to place a part of the body adjacent the platform (e.g., the top 410 of the base 402). The open design is also convenient for cleaning of the apparatus.

Figure 5A:
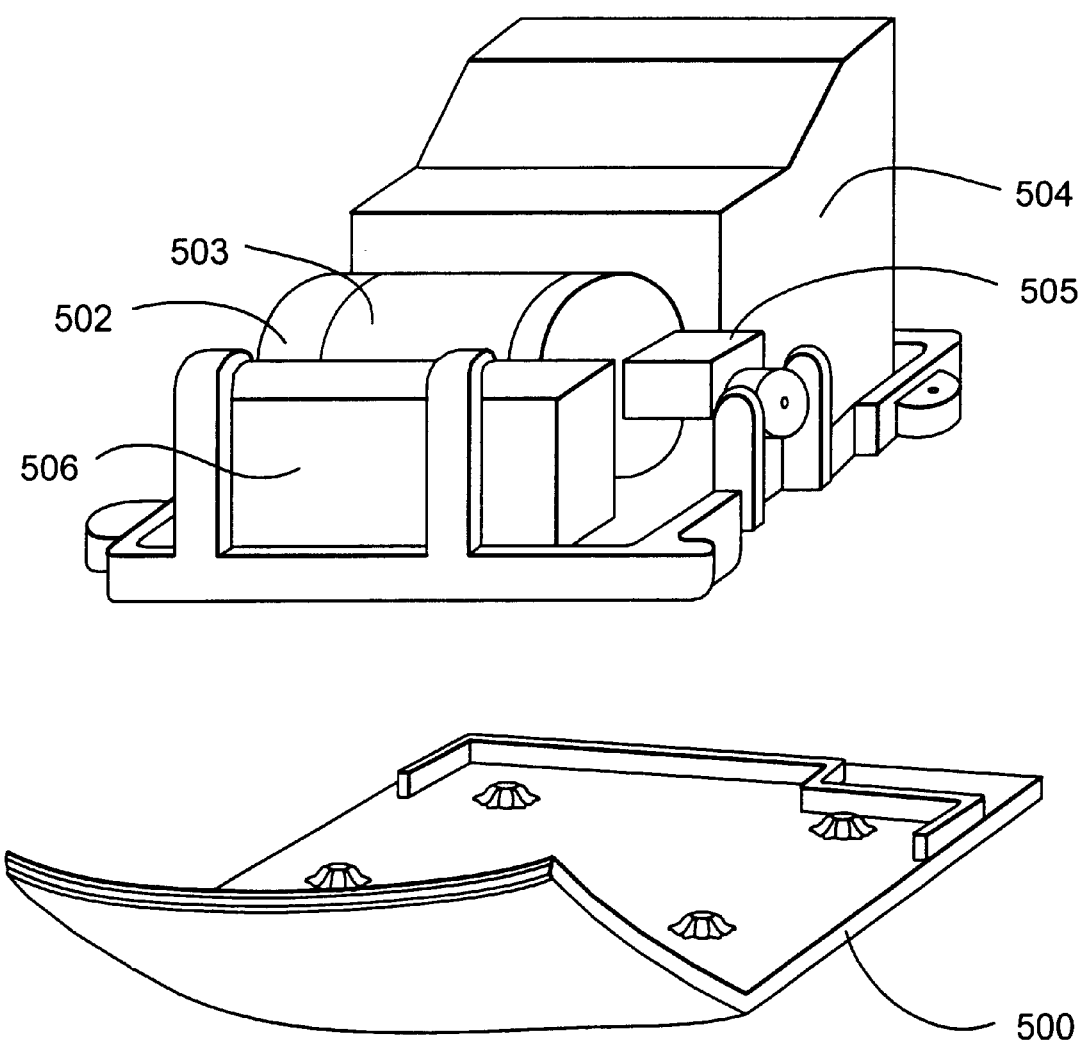
FIGS. 5A–5F illustrate the assembly of the apparatus illustrated in FIG. 4.

FIGS. 5A–5F illustrate the assembly of an apparatus having a rotatable drum within a housing as illustrated in FIG. 4. FIG. 5A illustrates the scanning system comprising a rotatable drum 502 with a storage layer radiation screen 503 mounted thereon, an image acquisition optical system 504 and an erasing mechanism 506 mounted on a base panel 500. Also illustrated is a rotation mechanism 505 for causing rotation of the drum 502. As can be seen, the image acquisition optical system 504 and erasing mechanism 506 are oriented relative to each other as illustrated in FIG. 1E.

Figure 5B:
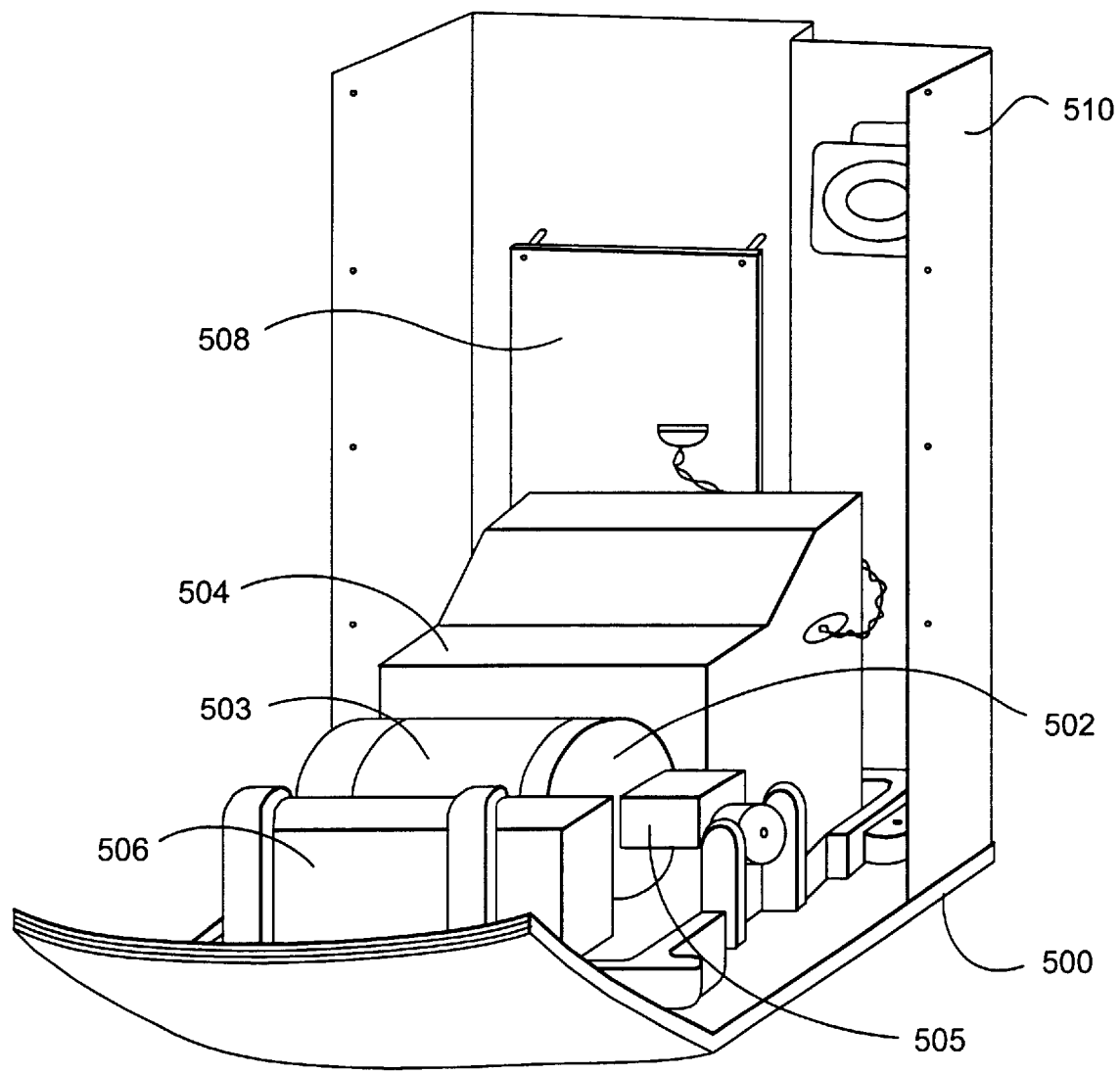

FIG. 5B illustrates a back panel 510 on which is mounted a data and image processing computer system 508. The computing system 508 is connected to the image acquisition system 504 such that image data captured by the scanning system can be transferred to the image processing computer system 508.

Figure 5C:
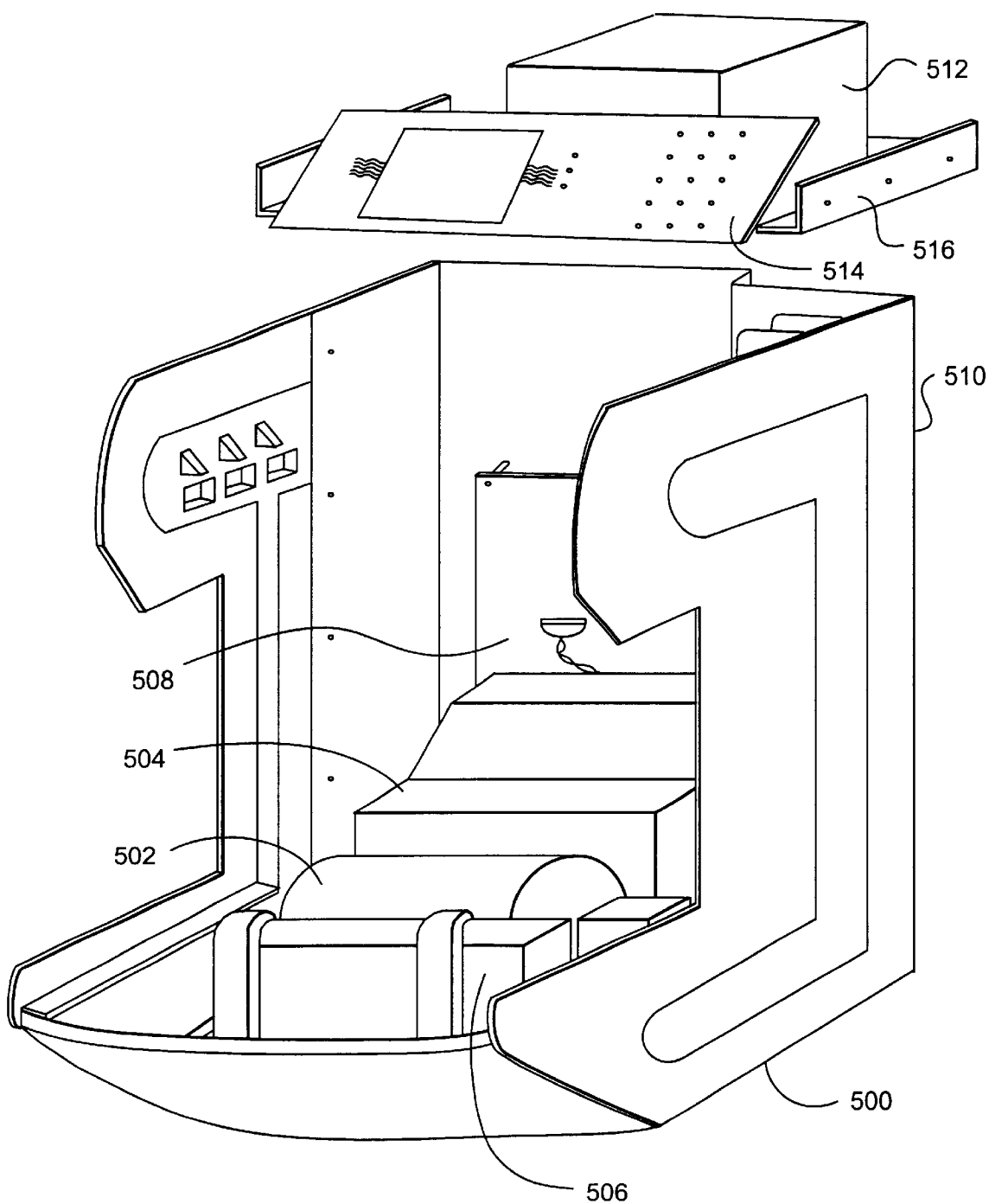

FIG. 5C illustrates the positioning of a top panel 516 onto the back panel 510. The top panel 516 includes a shielded electromagnetic wave energy source 512 (e.g., x-ray source) and an interactive display screen 514.

Figure 5D:
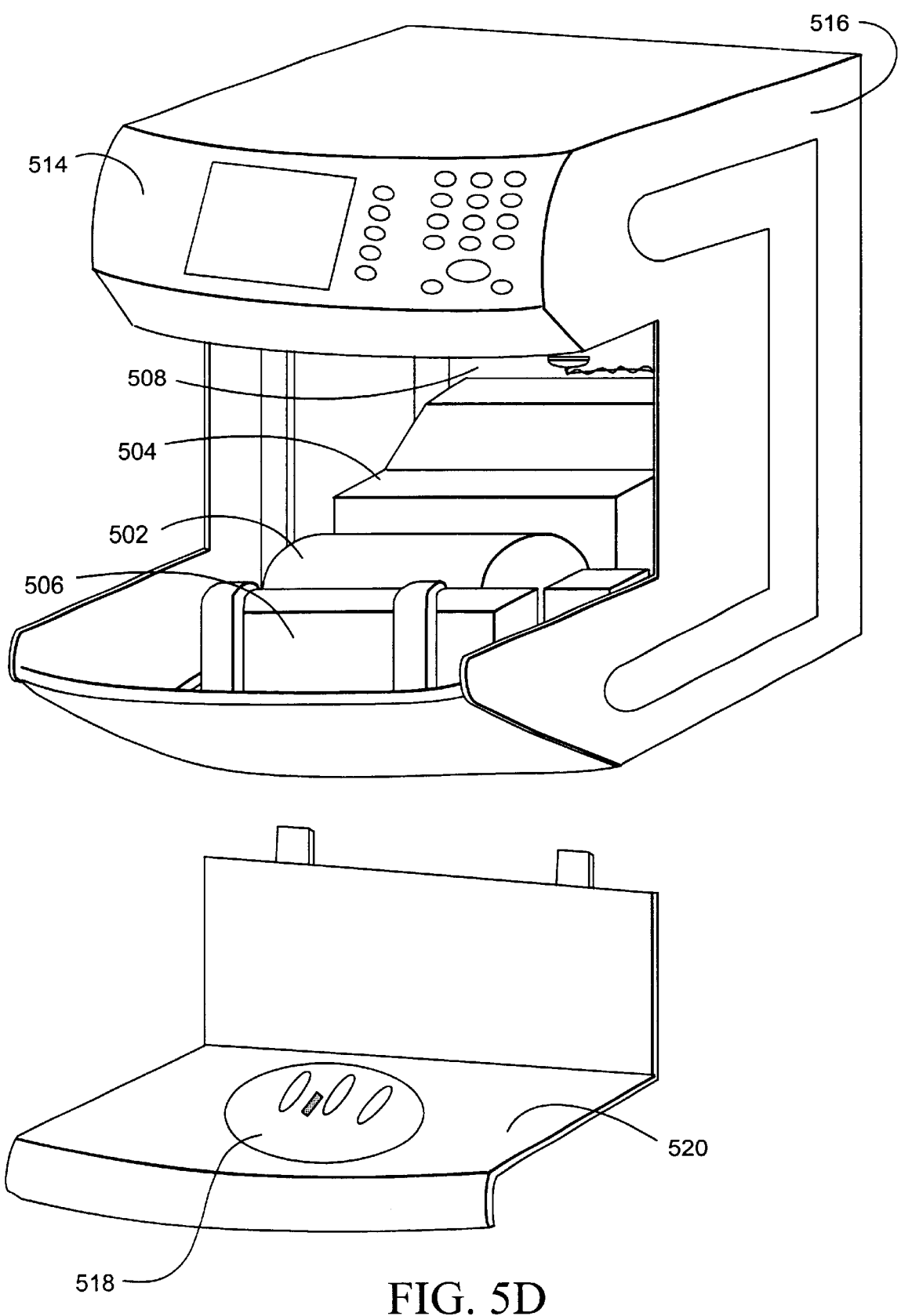

FIG. 5D illustrates the positioning of the throat panel 520 which forms a platform for the apparatus on which objects to be imaged may be placed. Positioned on the throat panel 520 is an object plate 518. The object plate 518 is positioned in a manner such that energy from the electromagnetic wave energy source within the top panel 516 passes through the object plate 518 and impinges on the storage layer screen 503 mounted on the drum 502.

Figure 5F:
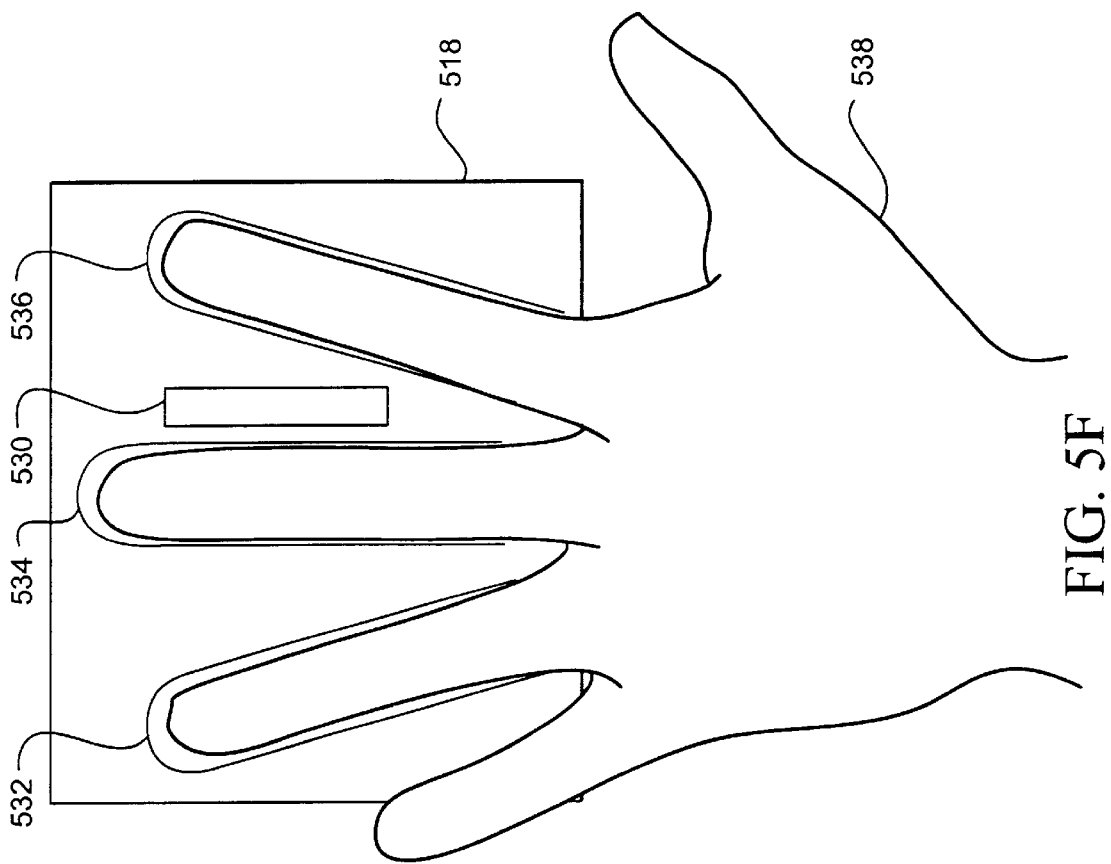
Figure 5E:
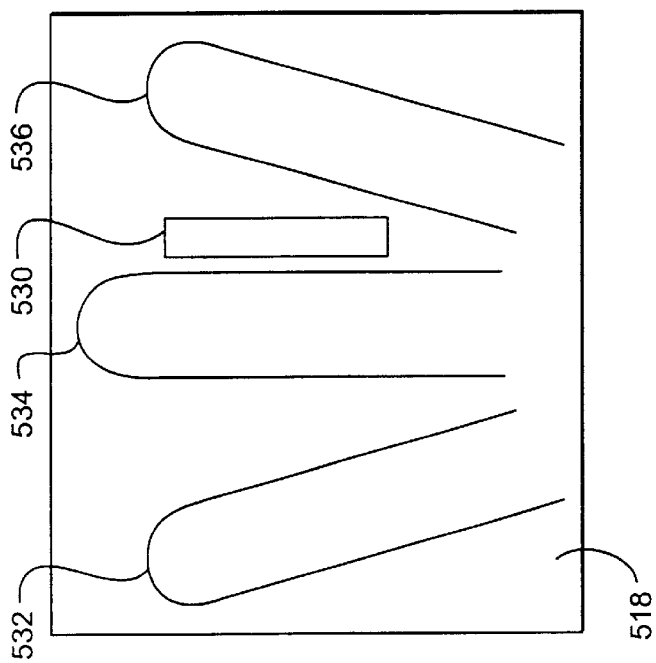

FIG. 5E is a top view of the object plate 518. The object plate 518 comprises an optically opaque but electromagnetic wave energy transmissive material. The object plate should not interfere with the electromagnetic wave energy reaching the storage layer screen and affect the image formed thereon. The object plate 518 includes guides 532, 534 and 536 provided for the middle three fingers of a patient's hand. Guides for different parts of the body may also be provided. In one embodiment, the object plate 518 is removable. The removability of the object plate 518 in combination with the open layout of the device allows the apparatus to be readily configured to be used with various different body parts.

A hard tissue reference is also illustrated in the object plate 518 shown in FIG. 5E. The hard tissue reference preferably includes a linear wedge 530 of a material with energy absorption characteristics similar to those of human bone. A preferred material for the wedge 530 is aluminum. The reference wedge 530 may have a known thickness profile which may be used to calibrate the system.

FIG. 5F illustrates the utilization of the object plate 518. As illustrated, the middle three fingers of a patient's hand 538 are placed over the guides 532, 534 and 536 on the object plate. This insures that the patient's hand is properly positioned relative to the energy source and the storage layer radiation of the screen when an image is formed.

Figure 6A:
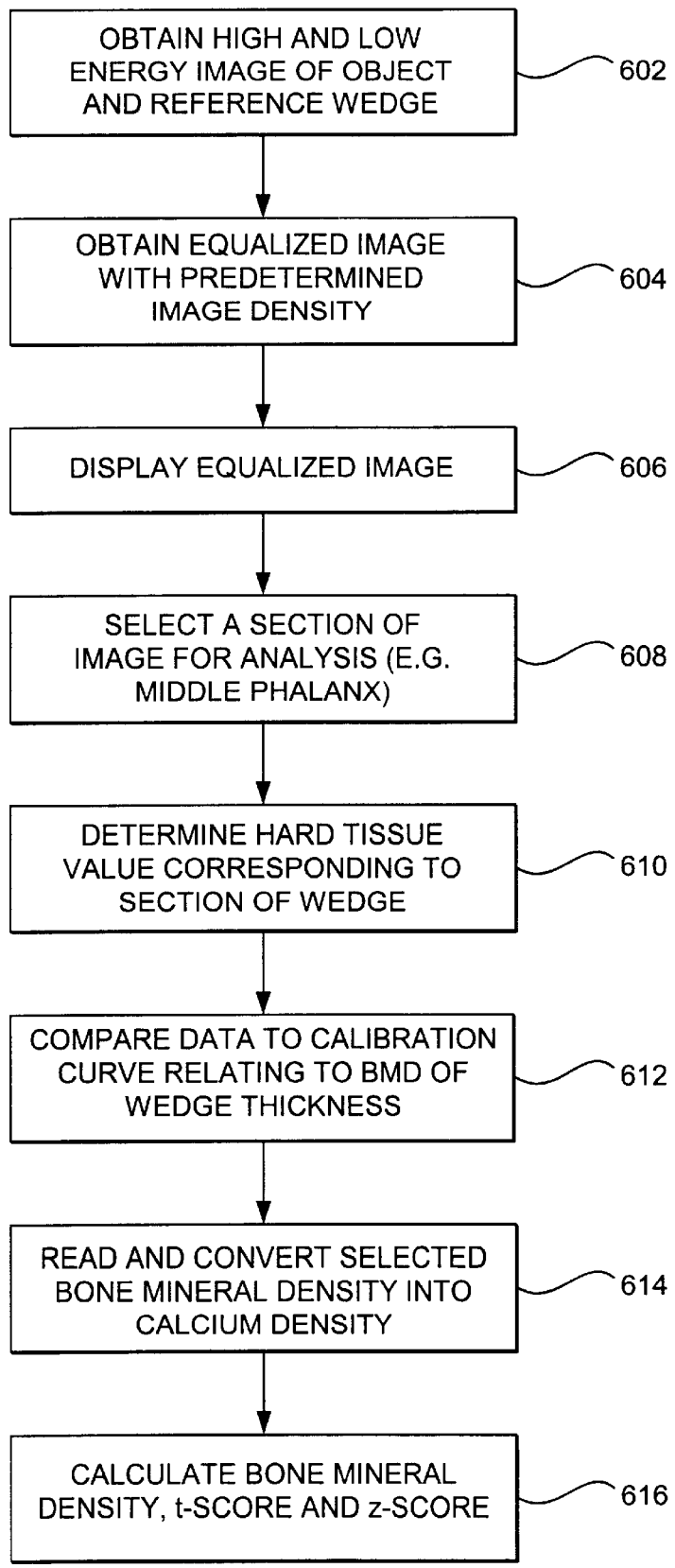
FIG. 6A illustrates a flow sequence of steps used in determining the bone mineral density of a patient.

FIG. 6A illustrates an example of a flow sequence for determining the bone mineral density (BMD) of a patient using dual energy x-ray absorptometry (DXA). In step 602, high and low energy x-ray images of a part of a patient's body and a reference wedge are formed on a storage layer screen, read and recorded by the apparatus. Preferably, the high energy image is formed using a 100 kV x-ray beam and the low energy is formed using a 44 kV x-ray beam. Preferably, the middle three fingers of the patient's hand are exposed. In step 604, equalized images of predetermined image density are formed for the high and low energy x-ray images. In step 606, the equalized images of the patient's fingers and the reference wedge may optionally be displayed on a user interface. In step 608, regions of the patient's fingers may then be selected for reading. Preferably, the middle phalanges of all of the middle three fingers are selected. Selection may be done manually by a technician or automatically by the apparatus. For example, the apparatus may automatically select the middle phalanx of all three of the patient's fingers and the technician may optionally alter the selections if visible anomalies are detected.

The hard tissue value of the selected section of the scanned image corresponding to a section of the reference wedge is determined 610, by the processing system. The data is compared 612, to a calibration curve relating the image density of a particular thickness of the wedge to the density of mineral component in human bone. The position in the bone image selected in the display is then converted 614, into the amount of bone mineral in accordance with the calibration curve. The calculated BMD is displayed 616, and further processed for t-scores and z-scores.

1. Normalization Using Reference Image

The present invention relies upon the use of radiographic absorptiometry (RA). Variability between images can occur due to variability in the x-ray source intensity, spectrum, and variations in film processing. A bone simulant (referred to herein as a reference wedge) has been used to compensate for these sources of variability. S. Yang, S. Hagiwara, K Engelke, et al., "Radiographic Absorptiometry of Bone Mineral Measurement of the Phalanges: Precision and Accuracy Study," Radiology, Vol. 192, No. 3, pp. 857–859, September 1994; C. Colbert, R. S. Bachtell, "Radiographic Absorptiometry (Photodensitometry)", in Non-Invasive Measurements of Bone Mass and Their Clinical Application, edited by Stanton H. Cohen. CRC Press, Inc. Boca Raton, Fla. 1981.

The use of a reference wedge to correct for the above described variabilities is based on a series of assumptions. First, the x-ray spectrum is assumed to consist of a single "effective" photon energy. No beam hardening, or preferential removal of the less energetic x rays from the beam is considered to occur as the x-ray beam passes through the hand or the aluminum wedge. The background optical density of the x-ray film is also assumed to be linearly related to x-ray exposure. The film's background optical density $D_o$ which is dependent upon the film's base density, emulsion, chemical fog, and x-ray scatter, is assumed to be uniformly distributed over the image and is therefore treated as a constant offset to the film density. The intensity of the film's exposure to radiation is also assumed to be uniform across the film. This is based on an assumption that radiation is directed parallel to the bone. The use of a reference wedge is also based on the assumption that the material of the reference wedge has an attenuation coefficient that is very close to that of the bone mineral that is being measured (typically aluminum 7075T6) and that soft tissue has a density and x-ray absorption close to water. It is also assumed that there is a straight line separation between attenuation due to soft tissue and attenuation due to bone.

Bone mineral density (BMD) has generally been calculated based on the following equation:

$$BMD = \frac{1}{\bar{\mu}_{Al}} \frac{1}{n} \Delta x \Delta y \sum_{i=1}^{n} \ln \frac{D_{wi} - D_o}{D_{(b+w)i} - D_o}$$

where $\mu$ bar is the average attenuation coefficient of aluminum $D_{wi}$ is the film optical density in the soft tissue region of the image;

$D_{(b+w)i}$ is the film optical density in the x-ray projection through both soft tissue and bone; and $D_o$ is the film's background optical density This equation relies upon the various assumptions that were outlined above.

It is noted that the attenuation coefficient, $\mu$, is a function of x-ray energy. In the above equation, an average attenuation coefficient, $\mu$bar, is employed. $\mu$bar is determined by making individual measurements along the length of the reference wedge and computing the attenuation coefficient at each sample based on the wedge thickness at that point. The attenuation coefficient $\mu$bar is thus the average of the measured attenuation coefficients. That averaged attenuation coefficient is employed across the entire image. As will be explained herein, the need to calculate an averaged attenuation coefficient using a reference wedge may be advantageously replaced by the use of a reference image and a normalization of an image pixel by pixel.

In the above equation, all the variables on the right hand side of the equation can be measured from the image of the reference wedge and the hand. BMD represents areal bone mineral density and is expressed in arbitrary units.

Applicants have realized that there are several difficulties with the assumptions that are made in support of using the above equation. For example, the notion of a single, "effective," photon energy for a polychromatic spectrum may be an over simplification in some cases. RA, as currently practiced, only specifies the peak kilovoltage (kVp) of the x-ray exposure. Depending on the beam filtration, which is not specified, the spectral properties of the x-ray beam can vary widely, and thus the differential between bone and soft tissue can change fairly dramatically. RA attempts to ameliorate this effect by normalizing the measurements with the attenuation coefficient of a reference material. However, the attenuation coefficient must be deduced from measurements which are uncertain, in terms of both the stochastic nature of x-ray photon production and recording, as well as geometric factors in determining the actual thickness of the reference wedge. For example, a 1% error in the estimate of x-ray transmission by the wedge at any given location, and a 0.1-mm shift in the position of the sampling grid relative to the reference wedge, leads to an underestimate of the attenuation coefficient of the reference wedge by nearly 4%. This underestimate translates directly into an overestimate of approximately the same magnitude of the BMD.

There is a relatively narrow range, often referred to as the dynamic range, of x-ray exposures to which x-ray film responds linearly. However, chemical film processing, the x-ray spectrum, and the variable output of the x-ray source, all affect the film response, and all can vary widely and unpredictably. RA accounts for this by digitizing the films, and digitally correcting the densities in the shadow of the reference wedge to known values. However, if the dynamic range of the film is exceeded, or if, the x-ray intensity varies sufficiently across the image, it becomes impossible to fully linearize the film response in this manner. This effect limits the accuracy that can be obtained with RA. Furthermore, given the variability in film processing and its strong effect on film response, the precision or repeatability of RA is limited.

The above equation also assumes that film fog, x-ray scatter, and the incident x-ray intensity all combine to contribute a constant background offset to the image, which is corrected for by $D_o$ in the equation. Film fog is believed to contribute a constant offset. X-ray scatter, while far from constant over the field of the image, is believed to be a relatively small effect, given the relatively short x-ray path length through the hand. More important is the variation in the x-ray field due to the heel effect. Both the field intensity and the mean x-ray energy can vary widely across the image, making it difficult to obtain uniform measurements from system to system. RA cannot account for this effect, but does avoid it somewhat by specifying a relatively large source-to-film distance so that the film subtends a relatively small solid angle of the x-ray beam and variations are minimized. Nevertheless, RA remains limited in that source-to-film distances must remain quite large—eliminating the possibility of developing a more compact system.

As a result, of the above-described variabilities, Applicants recognized that images do not have a constant background and it is thus disadvantageous to rely upon the assumption that the background is constant. These variabilities also reduce the validity of the assumption that film density is linearly related to x-ray intensity.

The x-ray spectrum is also not monoenergetic. Because the spectrum is not specified, the relative ratio of the attenuation of soft tissue to that of bone varies from system to system. Attempts to normalize this effect using the mean attenuation coefficient of a reference wedge of a bone-like substance (typically an aluminum alloy) rely on the ability to accurately measure the object and know its thickness at the location of any given measurement. It can be shown that small variations in that measurement or in the estimate of the wedge thickness, translate into relatively large variations in the mean attenuation coefficient, which in turn translate into comparable variations in the estimate of BMD.

Other than for a fairly narrow range of intensities, the optical density of film is not linearly related to exposure. Given all of the variables described previously, this further diminishes the reliability of achieving accurate and precise results using the RA technique.

Finally, because there are no "point-of-exam" diagnostics to ensure that a valid exam was taken, two x-ray exposures of the patient are currently produced. If, upon analysis, they differ by more than 2%, the exam is deemed to have failed.

Applicants now describe how various features of the present invention address the above described difficulties with RA and enable variability between images to be reduced.

One feature of the present invention is the use of storage layer phosphor screens, a photostimulable phosphor (storage phosphor) detector and digital image storage instead of film. Unlike film, storage phosphor responds linearly to exposure over several orders of magnitude. By using storage layer phosphor screens, variabilities that arise due to the limited dynamic range of film, the variations in film processing, and variability in the x-ray exposure are reduced. As a result, the assumptions underlying the above equation are more valid when storage layer radiation screens are employed. Specifically, as shown in the above equation, the heart of the measurement is a ratio. With a linear detector, that ratio is insensitive to the absolute level of exposure. The only concern becomes using enough x rays to optimize image signal-to-noise ratio with patient dose and exposure time.

A further feature of the present invention is the use of a reference image. Periodically (for example once each day) a reference image may be obtained with no object in the x-ray field of view. The reference image may be stored in the memory of the device. Each image subsequently obtained may be normalized by dividing, pixel by pixel, by the reference image. This procedure removes any fixed non-uniformities in the x-ray field, in the detector's response, or due to the hand support plate. This ensures that the values recorded in the normalized image arise only from attenuation due to object being imaged. Automatic diagnostic tests are performed on each reference image and on each patient image, thus eliminating the need for a second patient exposure for quality control purposes.

Use of the reference image to normalize images that are taken mostly remove the need for background correction. The scatter component remains, but in practice, seems to have a small effect. Moreover, the need for a large source-to-detector distance for minimizing intensity gradients in the x-ray field is eliminated by the normalization. As a result, use of a reference image enables more compact system geometries to be achieved.

A further feature of the present invention is the use of an integrated x-ray source and detector, as well as an embedded computer system with non-volatile memory. This enables the x-ray beam quality to be specified and assured at the factory, prior to installation at a customer site. In particular, the x-ray source may be much more tightly controlled, and, because the storage phosphor detection sub-systems (including image plates, the optics module, and electronics) are essentially uniform, inter-system variability is significantly reduced. In addition, by measuring each system's response to a known, standardized set of test objects, the gain and offset of each system can be set at the factory, thus ensuring that each system produced will provide highly similar results on the same object.

By taking the above described measures to reduce system to system variability, it is feasible to use multiple machines since the variability in the normative population data gathered in clinical trials is due almost entirely to population variation and not to machine-to-machine variability. Thus, the scores provided by the devices are more sensitive to bone density changes.

The use of a reference image enables images to be normalized pixel by pixel. As was noted above, the reference wedge is used to determine an average attenuation coefficient, $\mu$bar. By normalizing images pixel by pixel, the need for a reference wedge is eliminated.

A further feature of the present invention is the use of filtration to harden the x-ray spectrum. As a result, the difference in absorption characteristics by soft tissue and bone is more tightly controlled, thus making the ratio used in the above equation more repeatable, and the straight-line approximation to the soft tissue component more predictable.

In view of these modifications to the traditional RA approach, the present invention is able to employ the following equation to determine bone mineral density:

$$BMD = \frac{1}{n} \Delta x \Delta y \sum_{i=1}^{n} \ln \frac{I_{wi}}{I_{(b+w)i}}$$

where $I_{wi}$ is absorption in the soft tissue region of the image;

$I_{(b+w)i}$ is absorption in the bone region which includes soft tissue

It is noted that the $1/\mu$ term is eliminated since the measured values are actually intensities. As a result, no assumptions need to be made regarding whether there is a linear relationship to intensity.

Figure 6B:
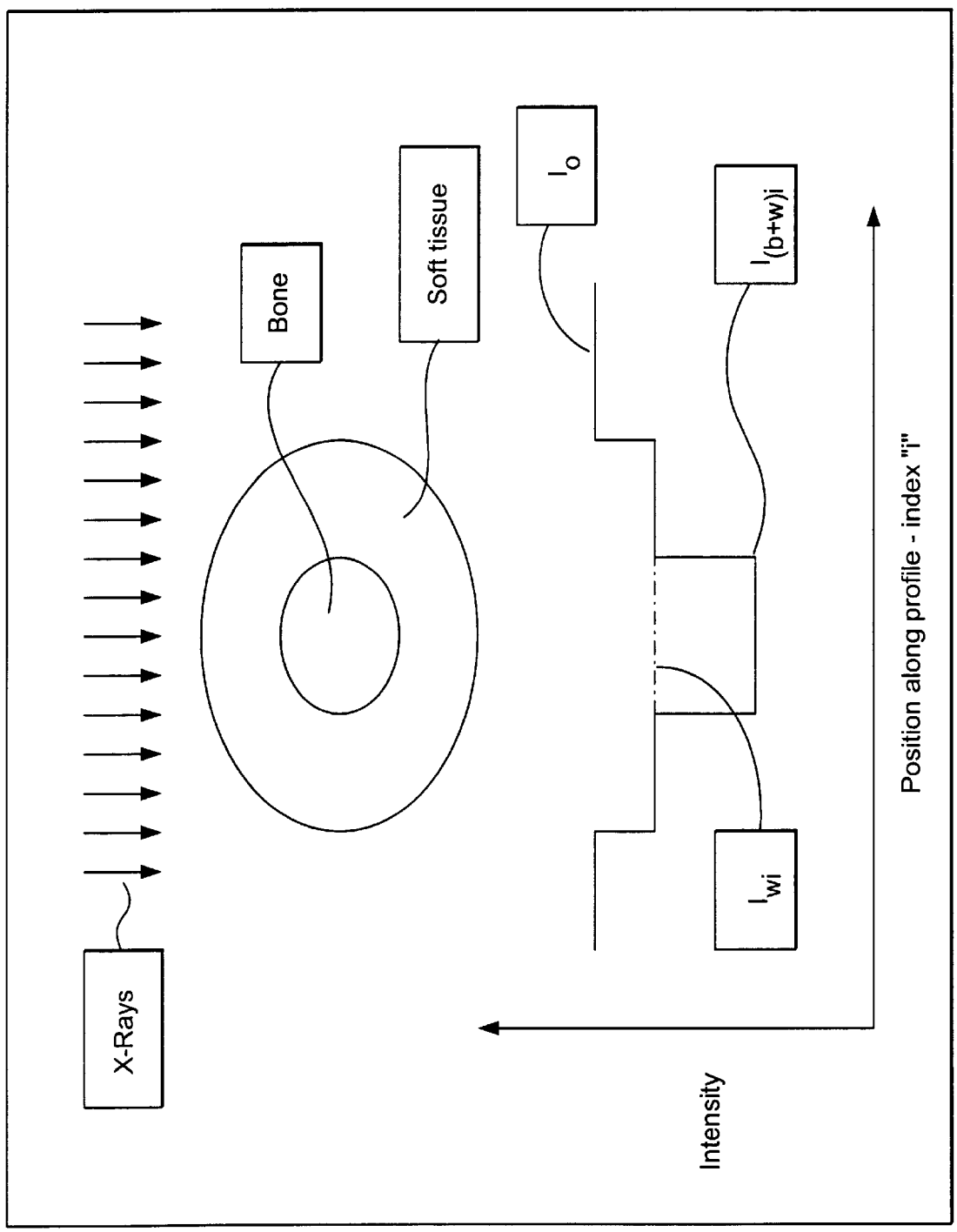
FIG. 6B is a stylized intensity profile across a bone in the finger which shows the regions used to calculate $I_{wi}$ and $I_{(b+w)i}$.

FIG. 6B is a stylized intensity profile across a bone in the finger which shows the regions used to calculate $I_{wi}$ and $I_{(b+w)i}$. Many of these profiles would be pooled to provide the overall BMD in a given phalanx. Note that there are a number of ways of summing and averaging the values. When an ensemble of profiles are combined, it may be more computationally efficient, and more mathematically precise to sum over all profiles and then average.

2. Correction of Geometric Distortion

In regard to embodiments of the present invention where the storage layer radiation screen is mounted on a rotatable drum, it is noted that the latent radiation image of the object is formed on a curved surface, e.g., the curved storage layer radiation screen. This causes the image on the screen to be distorted relative to the relatively planar object. The apparatus of the present invention includes logic which addresses this issue such that the relatively planar image, once read from the curved screen, is modified to correct for the curvature of the screen.

Figure 7B:
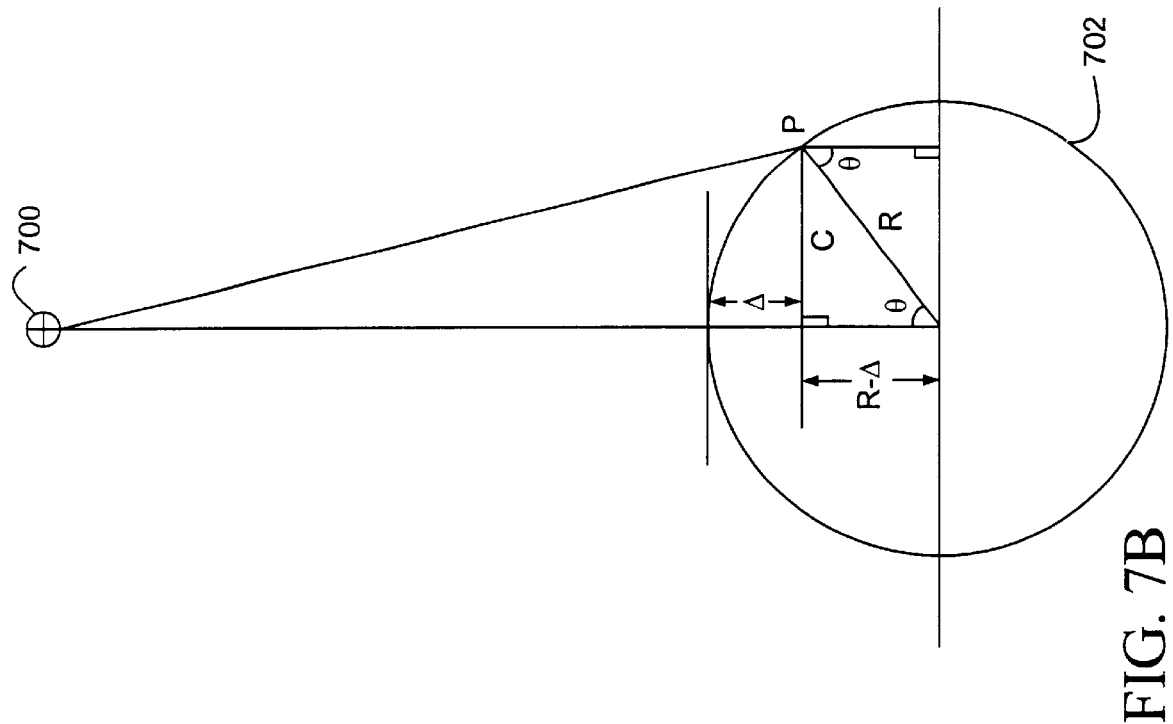
FIG. 7B also illustrates a curvature correction calculation for a drum mounted screen.
Figure 7A:
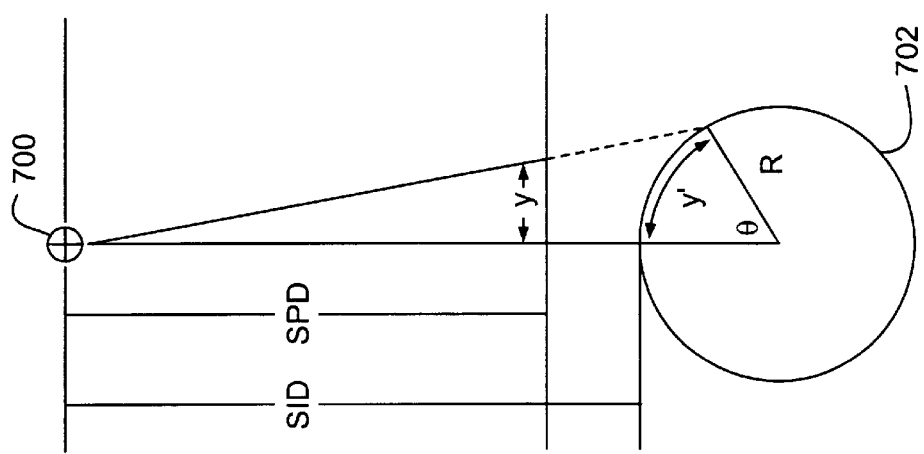
FIG. 7A illustrates a curvature correction calculation for a drum mounted screen.
Figure 7C:
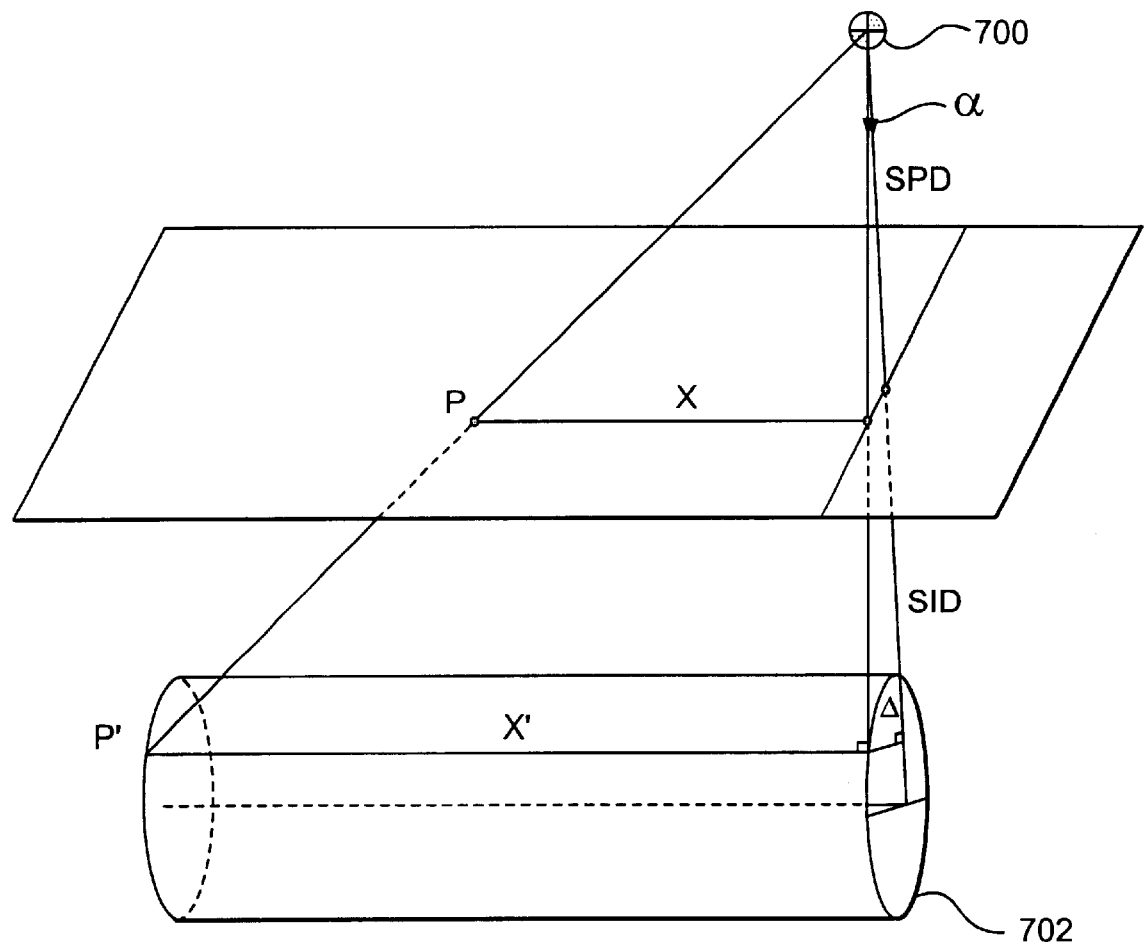
FIG. 7C illustrates a depth correction calculation for a drum mounted screen.

FIGS. 7A–7C illustrate a method of constructing a flat image of an object from a recording made on a curved storage layer radiation screen. The apparatus of the present invention includes logic for correcting for screen curvature based on the below calculations.

As used in the figures,

SID=source to image distance

SPD=source to platform distance

R=radius of drum

X'=surface distance in axial direction
X=platform equivalent of X'
Y'=surface distance on drum, θ direction to point P
Y=platform equivalent of Y'
θ=angle of Y' subtend FIGS. 7A–7B illustrate the geometry of projecting the image of a flat object formed from a point source on to a surface of a drum. The image formed of the object by a point source 700 results in a distortion in X which is a function of X' and Y'.

Under boundary conditions, when Y'=0, $$X = X' \frac{SPD}{SID} \text{ or, } X' = X \frac{SID}{SPD}$$

and when Y'=0, X'=X.M, where M is a magnification factor.

M is a function of Y', R, SID and SPD, and $$M = \frac{SID + \Delta}{SPD}$$

by simple geometry.

From FIG. 7B, $$\cos\theta = \frac{R - \Delta}{R}$$

therefore, $\Delta = R(1 - \cos\theta)$.

Thus, $$M = \frac{SID + R(1 - \cos\theta)}{R}$$

Since θ=Y'/R, in radians, $$M = \frac{SID + R\left(1 - \cos\frac{Y'}{R}\right)}{SPD}$$

and therefore, $$X = X' \frac{SPD}{SID + R\left(1 - \cos\frac{Y'}{R}\right)}$$

Thus when Y'=0, X=X'(SPD/SID) as predicted under boundary conditions.

Also, as shown in FIGS. 7A–7C, the distortion in Y is a function of Y' only. Using similar triangles from FIG. 7C, and comparing to the dimensions shown in FIG. 7B, $$\frac{C}{SID + \Delta} = \frac{Y}{SPD}$$

Also, C=R.sin θ and therefore $$Y = \frac{R \cdot \sin\theta \cdot SPD}{SID + R \cdot (1 - \cos\theta)} = \frac{SPD \cdot \sin\left(\frac{Y'}{R}\right)}{\frac{SID}{R} + 1 - \cos\left(\frac{Y'}{R}\right)}$$

Verification that the solution for X is complete is carried out by considering point P on the platform that projects to point P' on the drum as illustrated in FIG. 7C. By similar triangles, $$\frac{X}{X'} = \frac{SPD \cdot \sec\alpha}{(SID + \Delta) \cdot \sec\alpha}.$$

By cancellation of sec α, the same solution as developed from FIGS. 7A–7B results:

$$\frac{X}{X'} = \frac{SPD}{SID + \Delta}$$

3. Graphical User Interfaces

FIGS. 8A–8M provide a sequence of graphical user interfaces which illustrate an embodiment of session in which bone mineral density is determined using the apparatus of the present invention.

Figure 8A:
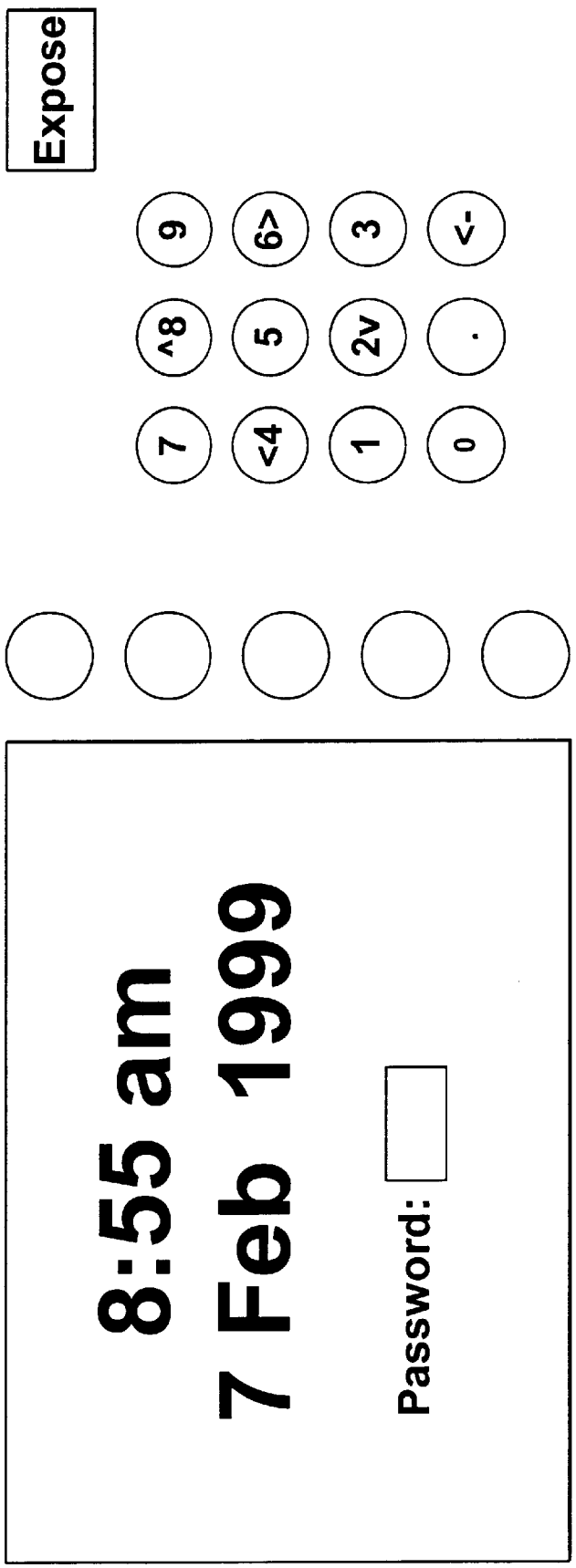

FIG. 8A illustrates a user interface which may be displayed prior to a user loging on to the apparatus. As illustrated, the display may show basic information such as the date and the time and may request a password to be input in order to gain access to the password protected apparatus.

Figure 8B:
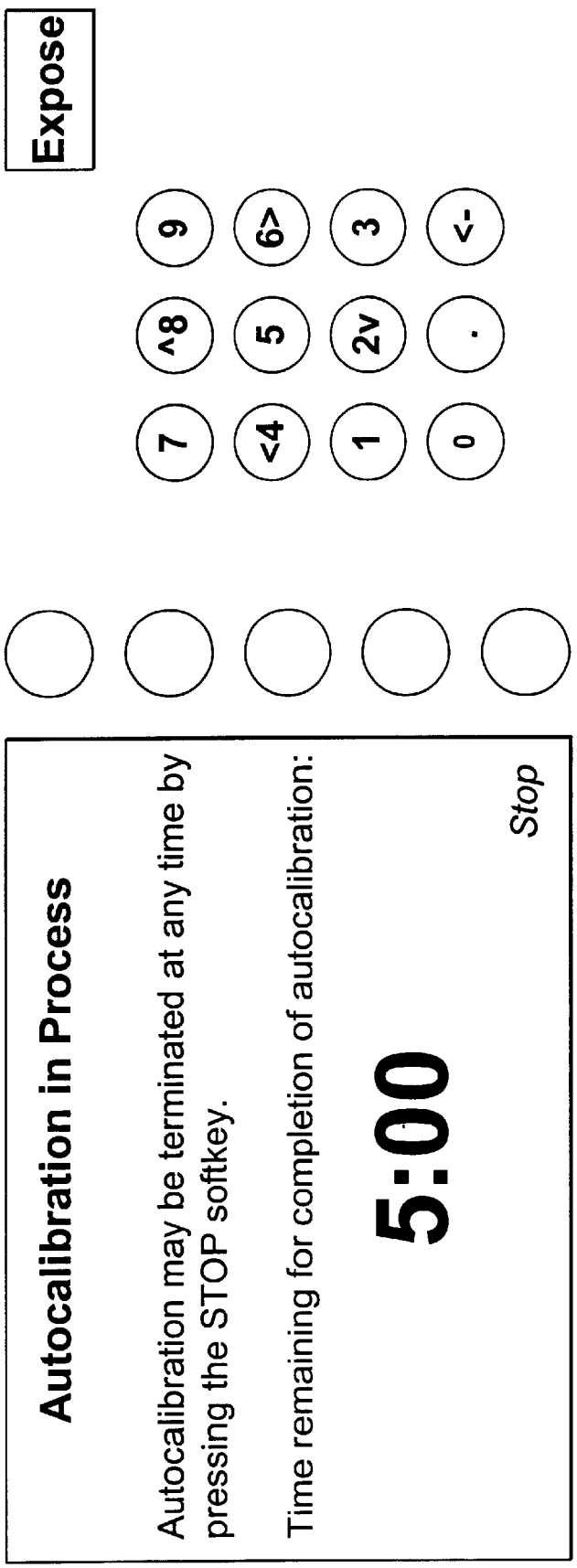

FIG. 8B illustrates a user interface which may be shown during autocalibration of the instrument. Autocalibration may be performed any time the apparatus is turned on and periodically therafter.

Figure 8C:
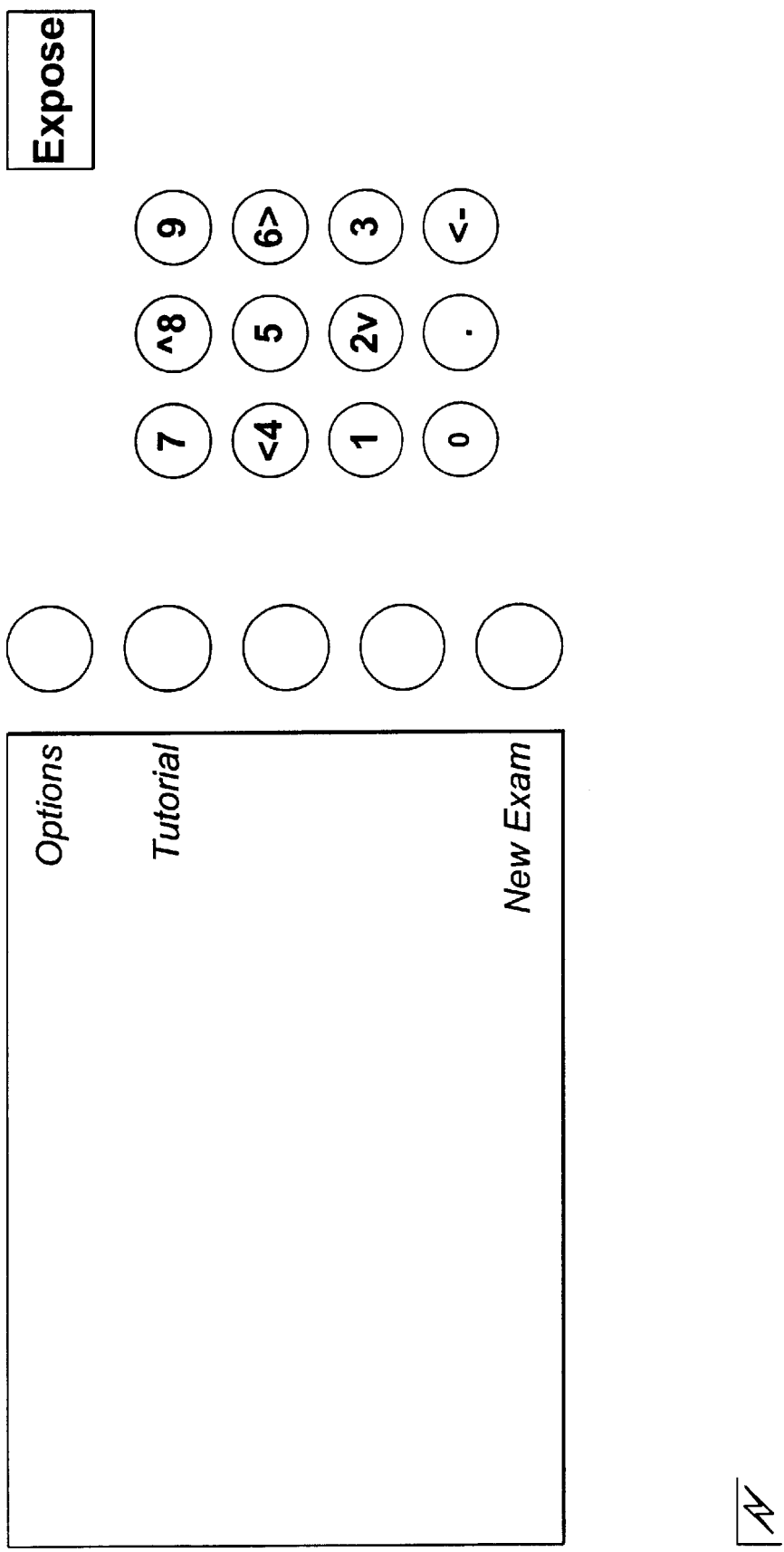

FIG. 8C illustrates a user interface which shows some of the options available to the user for the operation of the instrument. In addition to commencing a new examination of a patient, tutorials for training technicians in the operation of the instrument may also be available and other forms of information may be accessed via this interface.

FIG. 8D illustrates a user interface which may be displayed when a new examination is ready to be conducted. The user interface may display input areas for various forms of patient information. For preexisting patients, all or a portion of the patient information may already have been stored in the apparatus or a memory device associated with the apparatus.

FIG. 8E illustrates a user interface which allows the operator to review and modify patient data after it has been entered.

Figure 8F:
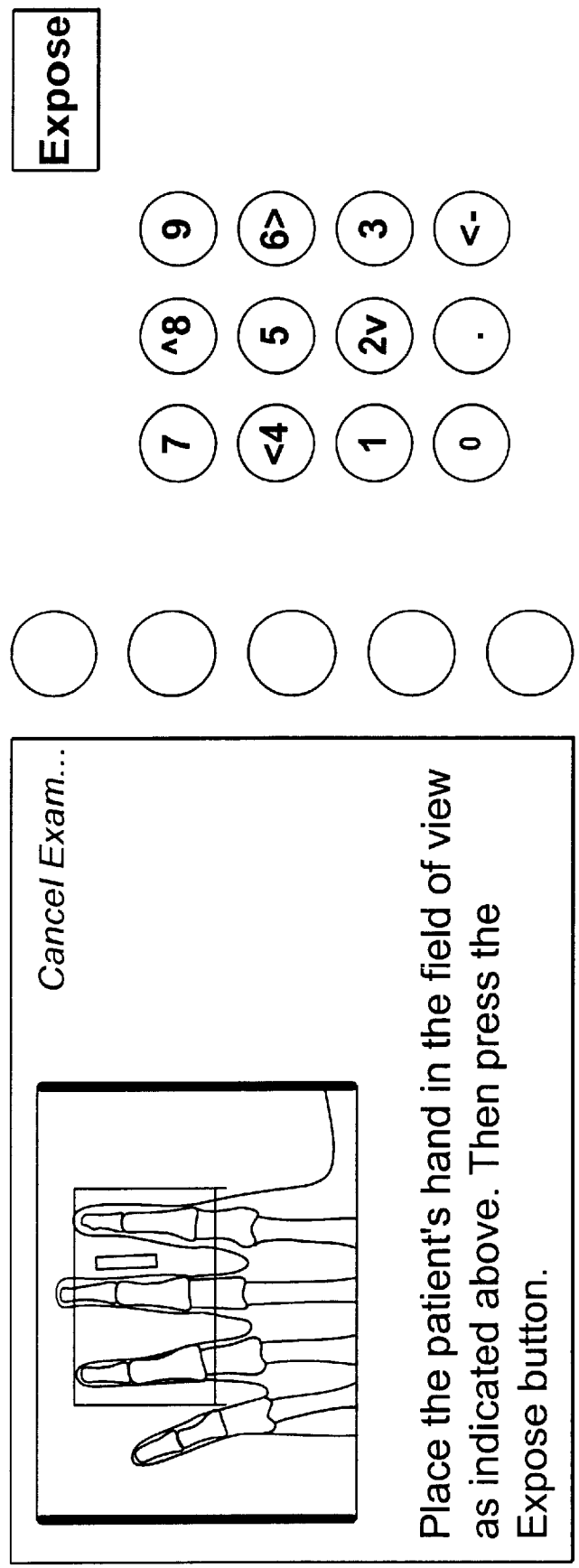

FIG. 8F illustrates a user interface which provides an instruction and visual guide regarding how to properly position a patient's hand for x-ray exposure. The figure also instructs the user how to cause an image to be taken.

Figure 8G:
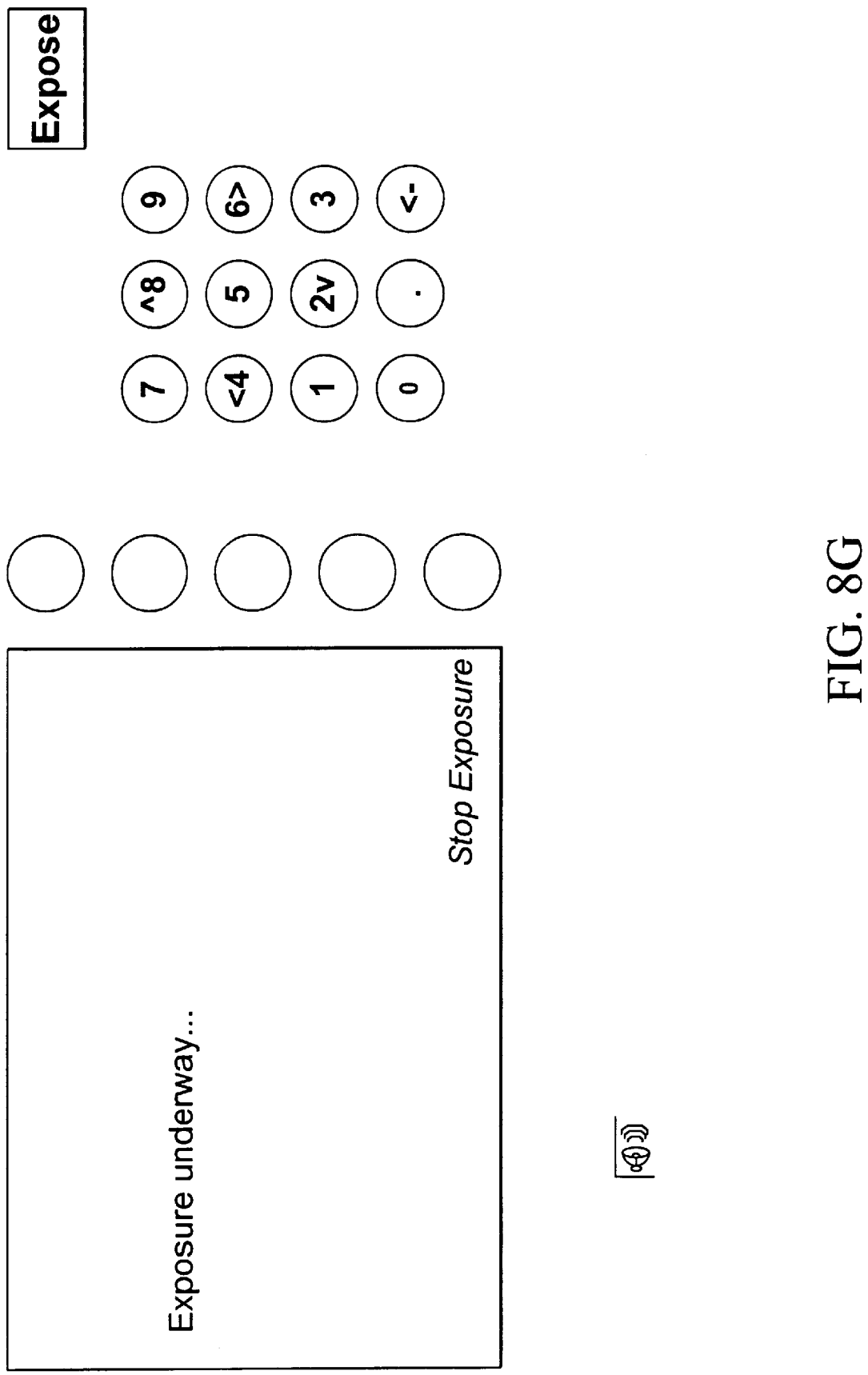

FIG. 8G illustrates a user interface which indicates that an exposure is being taken. Electromagnetic wave radiation is emitted by the radiation source at this time and a latent radiation image is formed on the storage layer radiation screen. During this time, the screen is stationary.

Figure 8H:
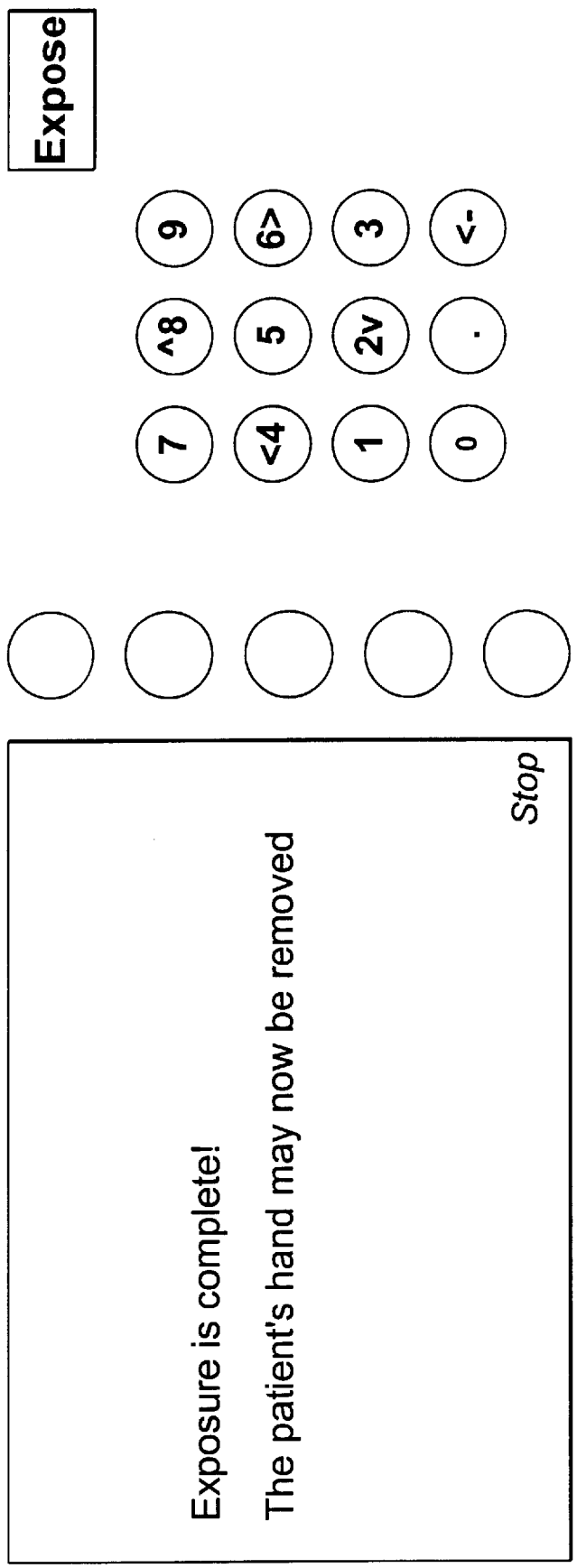

FIG. 8H illustrates a user interface indicating that the exposure is complete and directs the operator to remove the patient's hand from the apparatus. At this time, the apparatus is reading the radiation image formed on the storage layer radiation screen. During the time that the image is being read, the user interface may display various forms of information to the user such as background information, advertisements, etc. to occupy the user or technician as the image is read.

Figure 8I:
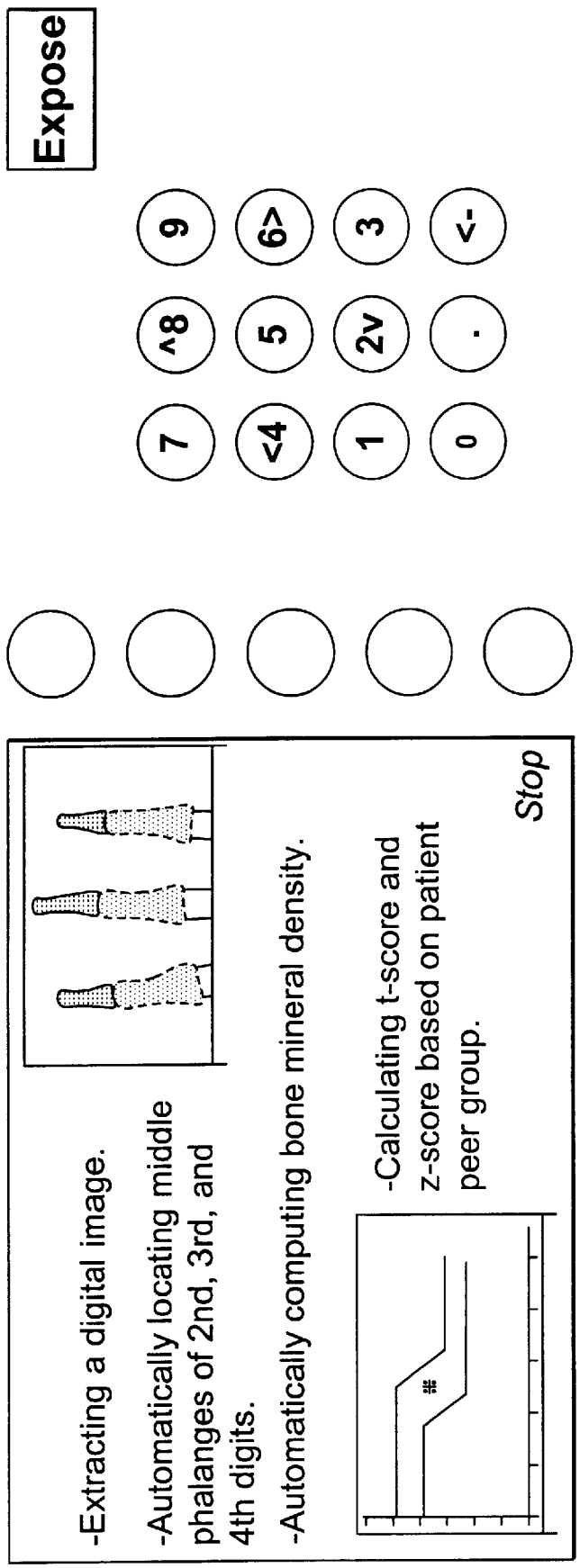

FIG. 8I illustrates a user interface that may be displayed once the image has been read. As illustrated, the apparatus may display a digital image. As also illustrated, the apparatus may automatically locates the middle phalanges of the middle three fingers, automatically computes the bone mineral density and calculates t-score and z-score based on the patient's peer group.

Figure 8J:
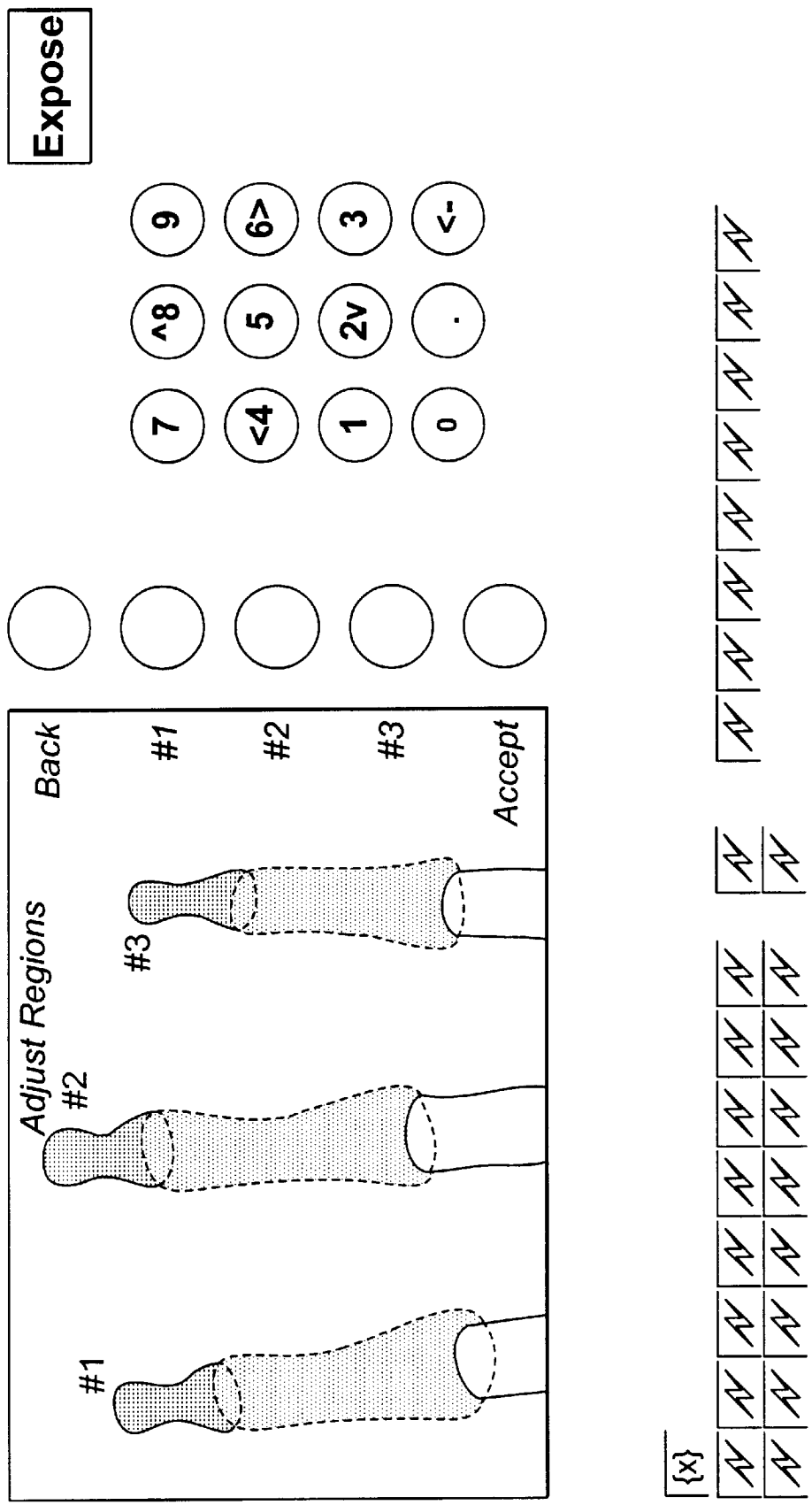

The apparatus may also indicate which parts of the image are going to be used to perform the analysis and may allow a technician to select a portion of the image on which to perform the analysis. FIG. 8J illustrates a user interface which allows a technician to select the portion of the image on which to perform the analysis. This allows the technician to avoid computing bone mineral density for regions where the hard tissue exhibits anomalous characteristics.

Figure 8K:
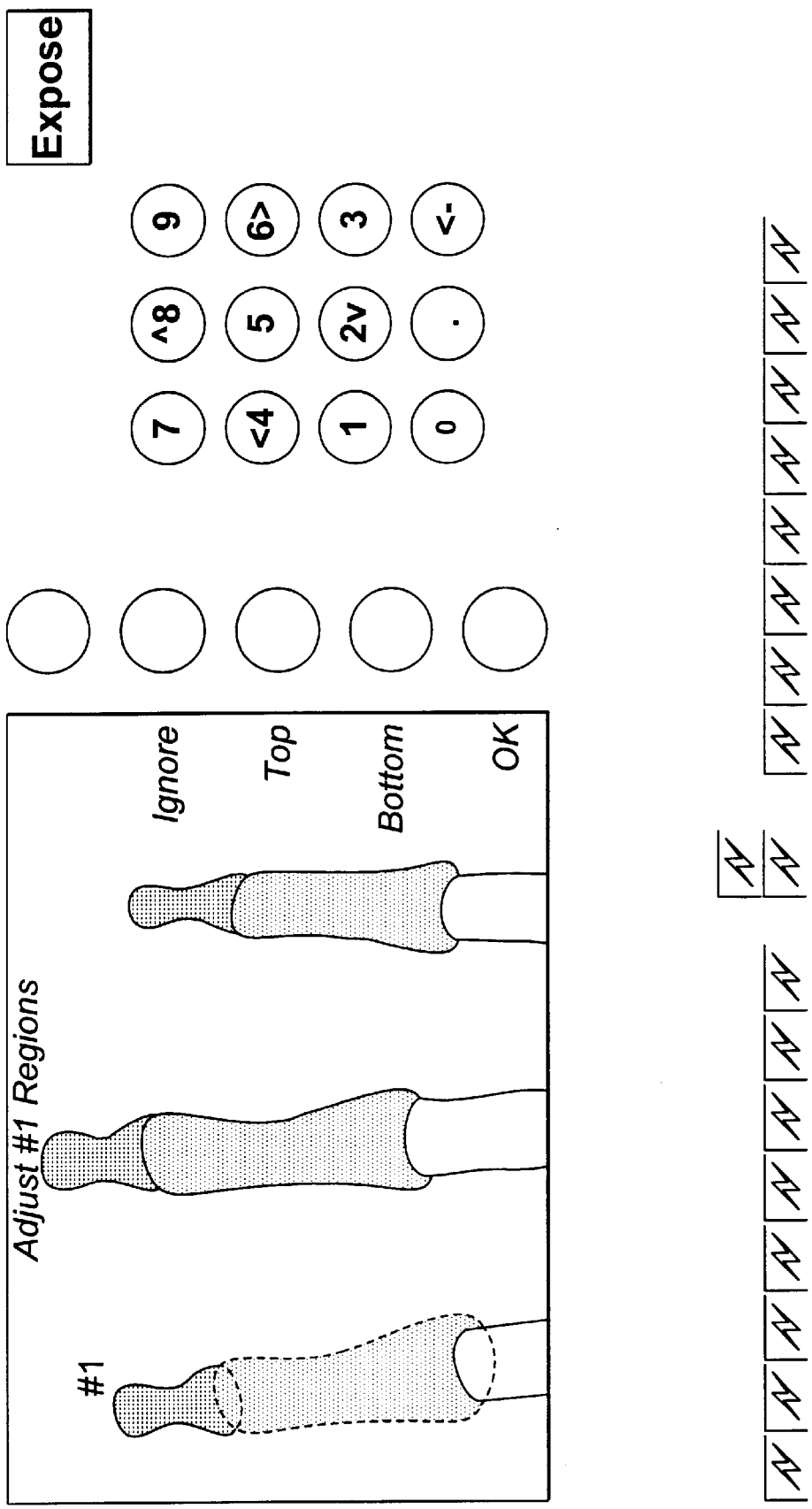

FIG. 8K illustrates a user interface which allows a technician to further select the portion of the image on which to perform a bone mineral density calculation.

Figure 8L:
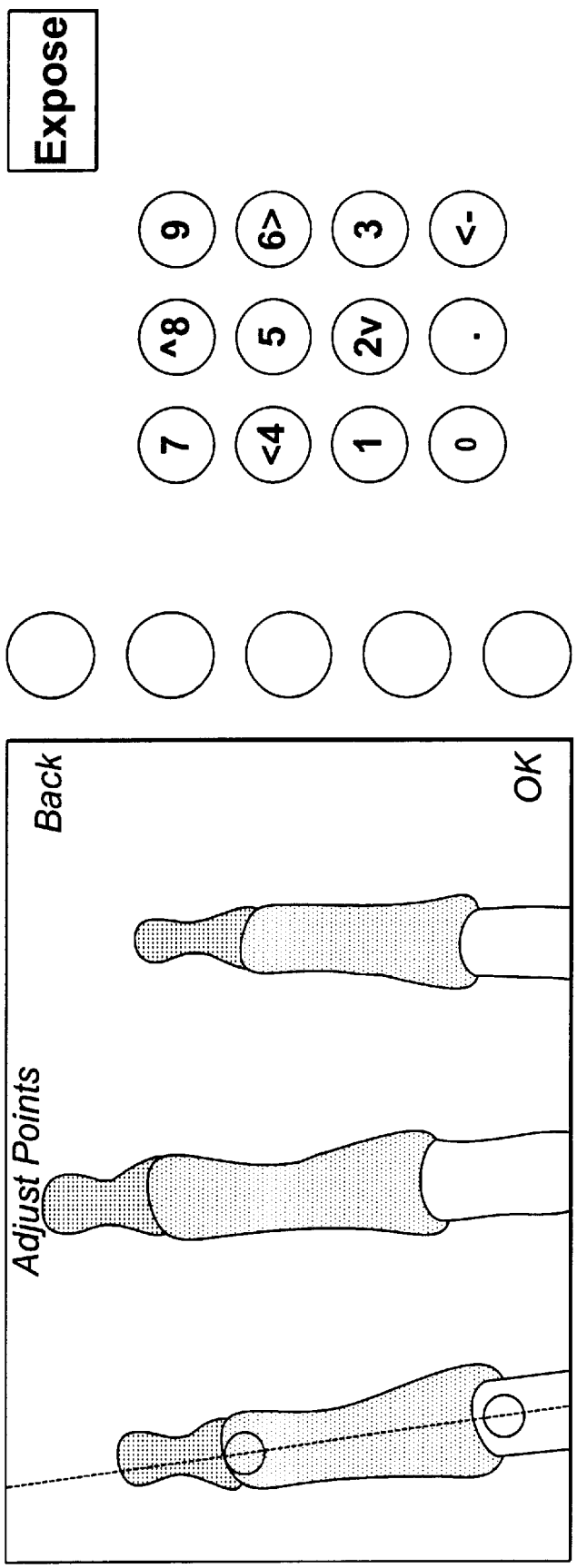

FIG. 8L illustrates a user interface which allows a technician to adjust the position of a line transecting one of the fingers on which a scan is to be performed.

Figure 8M:
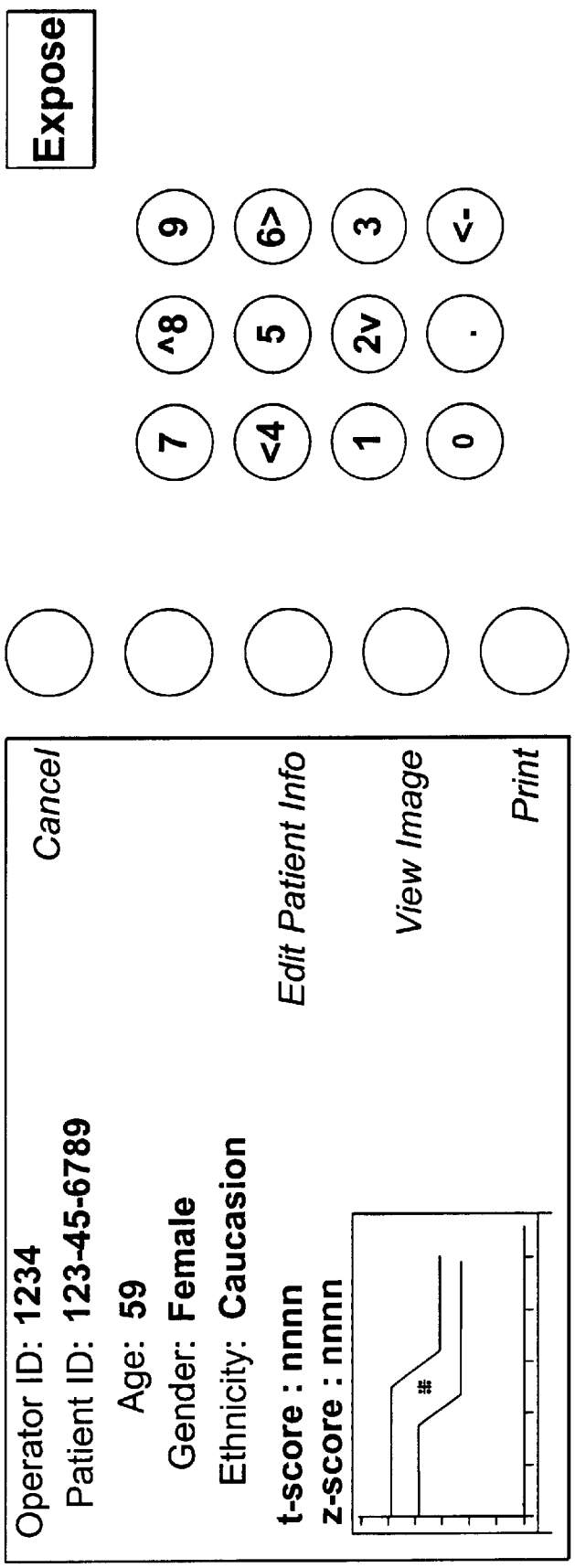

FIG. 8M illustrates a user interface which displays the final result of the bone mineral density scan. The screen display shows patient data as well as t-score and z-score based on bone mineral density measurements which can be printed out or stored in a computerized data storage system.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

We claim:

1. An apparatus for forming and reading a radiation image of an object which comprises:
   a base portion of the apparatus designed to be placed on a level surface such that the base portion supports the apparatus, the base portion of the apparatus comprising a storage layer radiation screen;
   an imaging system which reads the storage layer screen, and
   a mechanism for moving the storage layer radiation screen relative to the imaging system during reading of the storage layer screen; and
   a top portion of the apparatus comprising an electromagnetic wave radiation source,
   wherein
   the top portion of the apparatus is supported by the base portion in a spaced apart relationship above the base portion so as to define an aperture within which an object whose radiation image is to be taken may be positioned, and
   the electromagnetic wave radiation source is positioned relative to the storage layer radiation screen such that radiation from the electromagnetic wave radiation source which traverses the aperture and the object within aperture is absorbed by the storage layer radiation screen.

2. The apparatus according to claim 1 wherein the apparatus further includes a screen erasing mechanism for erasing the storage layer radiation screen.

3. The apparatus according to claim 1 wherein the electromagnetic wave radiation source delivers energy at a single energy level.

4. The apparatus according to claim 1 wherein the electromagnetic wave radiation source delivers energy at multiple energy levels.

5. The apparatus according to claim 1 wherein the apparatus further includes an object plate positioned adjacent the platform.

6. The apparatus according to claim 5 wherein the object plate comprises an optically opaque but electromagnetic wave energy transmissive material.

7. The apparatus according to claim 5 wherein the object plate comprises guides for the middle three fingers of a patient's hand.

8. The apparatus according to claim 5 wherein the object plate is removable from the platform.

9. The apparatus according to claim 5 wherein the object plate comprises a hard tissue reference.

10. An apparatus for forming and reading a radiation image of an object which comprises:
    a base portion of the apparatus designed to be placed on a level surface such that the base portion supports the apparatus, the base portion of the apparatus comprising a storage layer radiation screen having a non-planar surface;
    an imaging system which reads the storage layer screen, and
    a mechanism for moving the storage layer radiation screen relative to the imaging system during reading of the storage layer screen; and
    a top portion of the apparatus comprising an electromagnetic wave radiation source, the top portion of the apparatus being supported by the base portion in a spaced apart relationship above the base portion so as to define an aperture within which an object whose radiation image is to be taken may be positioned, the electromagnetic wave radiation source being positioned relative to the storage layer radiation screen such that radiation from the electromagnetic wave radiation source which traverses the aperture and the object within aperture is absorbed by the storage layer radiation screen; and
    computer executable logic which corrects distortion associated with reading a storage layer screen with a non-planar surface.

11. An apparatus for forming and reading a radiation image of an object which comprises:
    a base portion of the apparatus designed to be placed on a level surface such that the base portion supports the apparatus, the base portion of the apparatus comprising a storage layer radiation screen;
    an imaging system which reads the storage layer screen, and
    a mechanism for moving the storage layer radiation screen relative to the imaging system during reading of the storage layer screen; and
    a top portion of the apparatus comprising an electromagnetic wave radiation source, the top portion of the apparatus being supported by the base portion in a spaced apart relationship above the base portion so as to define an aperture within which an object whose radiation image is to be taken may be positioned, the electromagnetic wave radiation source being positioned relative to the storage layer radiation screen such that radiation from the electromagnetic wave radiation source which traverses the aperture and the object within aperture is absorbed by the storage layer radiation screen; and
    computer executable logic which is capable of
    taking data corresponding to a read storage layer screen and data corresponding to a reference image,
    normalizing the data corresponding to the read storage layer screen relative to the reference image, and
    computing bone mineral density based on the normalized data.

12. The apparatus according to claim 11 wherein the data corresponding to the read storage layer screen is normalized relative to the reference image pixel by pixel.

13. The apparatus according to claim 11 wherein the storage layer radiation screen has a non-planar surface, the computer executable logic further comprising logic for correcting for geometric distortion arising from the screen having a non-planar surface.

14. The apparatus according to claim 11 wherein the computer executable logic computes bone mineral density based on a ratio between absorption in a bone region and absorption in a soft tissue region.

15. The apparatus according to claim 11 wherein the computer executable logic computes bone mineral density based on the equation $$BMD = \frac{1}{n}\Delta x \Delta y \sum_{i=1}^{n} \ln \frac{I_{wi}}{I_{(b+w)i}}$$

where $I_{wi}$ is absorption in the soft tissue region of the image;

$I_{(b+w)i}$ is absorption in the bone region which includes soft tissue.

16. The apparatus according to claim 11 wherein the computer executable logic further includes logic for determining sections of an image upon which to compute bone mineral density.

17. An apparatus for forming and reading a radiation image of an object which comprises:

a base portion of the apparatus designed to be placed on a level surface such that the base portion supports the apparatus, the base portion of the apparatus comprising a storage layer radiation screen;

an imaging system which reads the storage layer screen, and a mechanism for moving the storage layer radiation screen relative to the imaging system during reading of the storage layer screen; and a top portion of the apparatus comprising an electromagnetic wave radiation source and a user interface for controlling selected operations of the apparatus, wherein the top portion of the apparatus is supported by the base portion in a spaced apart relationship above the base portion so as to define an aperture within which an object whose radiation image is to be taken may be positioned, and the electromagnetic wave radiation source is positioned relative to the storage layer radiation screen such that radiation from the electromagnetic wave radiation source which traverses the aperture and the object within aperture is absorbed by the storage layer radiation screen.

* * * * *